(12) United States Patent
Subramanian et al.

(10) Patent No.: US 9,295,456 B2
(45) Date of Patent: Mar. 29, 2016

(54) OCCLUSION DEVICE FOR CLOSING ANATOMICAL DEFECTS

(75) Inventors: Venkatraman Subramanian, Singapore (SG); Yin Chiang Freddy Boey, Singapore (SG); Yong-dan Tang, Singapore (SG); Wei Luen James Yip, Singapore (SG); Hong Duc Duong, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 13/576,927

(22) PCT Filed: Feb. 2, 2011

(86) PCT No.: PCT/SG2011/000049
§ 371 (c)(1),
(2), (4) Date: Oct. 15, 2012

(87) PCT Pub. No.: WO2011/096896
PCT Pub. Date: Aug. 11, 2011

(65) Prior Publication Data
US 2013/0030455 A1    Jan. 31, 2013

Related U.S. Application Data

(60) Provisional application No. 61/301,830, filed on Feb. 5, 2010.

(51) Int. Cl.
*A61B 17/08* (2006.01)
*A61B 17/00* (2006.01)

(52) U.S. Cl.
CPC ... *A61B 17/0057* (2013.01); *A61B 2017/00575* (2013.01); *A61B 2017/00597* (2013.01); *A61B 2017/00606* (2013.01); *A61B 2017/00615* (2013.01); *A61B 2017/00619* (2013.01); *A61B 2017/00623* (2013.01)

(58) Field of Classification Search
CPC ............... A61B 17/0057; A61B 2017/00575; A61B 2017/00623; A61B 2017/00619; A61B 2017/00597; A61B 2017/00615; A61B 2017/00606
USPC .......... 606/213, 215; 623/23.72, 23.75, 23.76
See application file for complete search history.

(56) References Cited

U.S. PATENT DOCUMENTS

| | | | |
|---|---|---|---|
| 5,425,744 A * | 6/1995 | Fagan et al. | 606/213 |
| 5,853,422 A * | 12/1998 | Huebsch et al. | 606/213 |
| 6,143,037 A | 11/2000 | Goldstein et al. | |
| 6,312,446 B1 * | 11/2001 | Huebsch et al. | 606/213 |
| 6,440,152 B1 * | 8/2002 | Gainor et al. | 606/213 |
| 6,949,116 B2 * | 9/2005 | Solymar et al. | 623/1.12 |
| 6,960,224 B2 * | 11/2005 | Marino et al. | 606/215 |
| 7,192,435 B2 * | 3/2007 | Corcoran et al. | 606/213 |
| 8,257,389 B2 * | 9/2012 | Chanduszko et al. | 606/213 |
| 2002/0183787 A1 * | 12/2002 | Wahr et al. | 606/213 |

(Continued)

*Primary Examiner* — Gregory Anderson
*Assistant Examiner* — Son Dang
(74) *Attorney, Agent, or Firm* — Seed IP Law Group PLLC

(57) ABSTRACT

The present invention generally relates to the field of transcatheter device closure techniques for closing an opening in a tissue and more particularly, to occlusion devices for closing anatomical defects in tissue. More particularly the present invention refers to occlusion devices for closing septal abnormalities such as atrial septal defects and patent foramen ovale, and to methods of closing an anatomical defect in a tissue.

60 Claims, 31 Drawing Sheets

(56) References Cited

U.S. PATENT DOCUMENTS

| | | |
|---|---|---|
| 2005/0070957 A1 | 3/2005 | Das |
| 2005/0113868 A1 | 5/2005 | Devellian et al. |
| 2005/0192627 A1* | 9/2005 | Whisenant et al. ............ 606/213 |
| 2005/0267524 A1* | 12/2005 | Chanduszko ................. 606/213 |
| 2006/0009800 A1* | 1/2006 | Christianson et al. ........ 606/213 |
| 2006/0122647 A1 | 6/2006 | Callaghan et al. |
| 2006/0217760 A1* | 9/2006 | Widomski et al. ............ 606/213 |
| 2007/0066994 A1* | 3/2007 | Blaeser et al. ................ 606/213 |
| 2007/0118176 A1 | 5/2007 | Opolski et al. |
| 2007/0123934 A1* | 5/2007 | Whisenant et al. ............ 606/213 |
| 2007/0293891 A1* | 12/2007 | Corcoran et al. ............. 606/213 |
| 2008/0051830 A1 | 2/2008 | Eidenschink et al. |
| 2008/0086168 A1* | 4/2008 | Cahill ........................... 606/213 |
| 2009/0036920 A1* | 2/2009 | Preinitz et al. ................ 606/213 |
| 2009/0076525 A1* | 3/2009 | Kato et al. .................... 606/139 |
| 2009/0143789 A1* | 6/2009 | Houser ......................... 606/142 |
| 2010/0041587 A1 | 2/2010 | Porter et al. |
| 2013/0165967 A1* | 6/2013 | Amin et al. ................... 606/213 |
| 2013/0289618 A1* | 10/2013 | Chanduszko et al. ........ 606/213 |

* cited by examiner

OCCLUSION DEVICE FOR CLOSING ANATOMICAL DEFECTS

FIELD OF THE INVENTION

The present invention generally relates to the field of transcatheter device closure techniques for closing an opening in a tissue and more particularly, to occlusion devices for closing anatomical defects in tissue and methods of closing an anatomical defect in tissue.

BACKGROUND OF THE INVENTION

Defects in tissue are often combined with an opening in a tissue such as in the blood vessel wall and organ tissues, like the septum in the heart of mammals, for example, atrial septal defect (ASD) and patent foramen ovale (PFO) as shown in FIG. 1. FIG. 1a shows normal septa between the right atrium (1) and the left atrium (2).

During the fetal development, the septum primum (3) starts to grow downward from the roof to divide the atria into two chambers, leaving a hole in the center called ostium secundum (4). A second septum, septum secundum (5), starts to develop on the right atrial side of the septum primum (3) and normally completely covers the ostium secundum (4) and, thereby resulting in a closed foramen ovale (6). However in some cases, incomplete coverage results in a hole (an opening) permitting blood flow in either direction (left-to-right or right-to-left), also known as an atrial septal defect. This atrial septal defect is also called secundum ASD (7). An example of such an atrial septal defect is shown in FIG. 1b. Even after normal formation of the septum secundum (5), an opening foramen ovale—remains between the septa in the fetus, functioning as a one-way (right-to-left) valve. This opening allows blood to follow from right atrium (1) to left atrium (2), bypassing the lungs in utero. At birth, changes in atrial pressures leads to apposition of the septa. Complete sealing of the opening happens within hours of birth. However, a patent foramen ovale, also called PFO (8), remains for about 25% of the total population. This situation is shown in FIG. 1c. ASD accounts for 25-30% of congenital heart defects that are diagnosed in adult hood, among which the majority are Secundum ASD (about 75%, located in the region of the fossa ovalis). The associated symptoms are most often exertional dyspnoea or fatigue and subsequent morbidity includes right ventricular dysfunction and failure, atrial tachyarrhythmias, or stroke. Clinical significance of PFO is still much debated; however, even a small, untreated patent foramen ovale can cause heart-related difficulties such as labored breathing or recurrent respiratory infections. Other medical conditions, such as migraine headaches, have also been associated with a PFO. PFO is also considered a possible risk factor for stroke and systemic embolism because of the potential formation of blood clots. These clots may form in veins and subsequently pass into circulation through the PFO, without being filtered in the lungs.

In general, treatment options include anticoagulant medication, surgical closure and transcatheter device closure. The anticoagulant therapy normally comprises the administration of aspirin, clopidogrel (Plavix), aspirin and clopidogrel together, and warfarin (Coumadin). Medication does not improve morbidity to a comfortable level and only reduces the risk of mortality. Surgical closure can be done safely and achieve extremely low mortality rate. But it does require open-heart surgery and an extracorporeal circulation system. Transcatheter closure is safe and effective for Secundum ASD and PFO. The entry is similar to a percutaneous cardiovascular intervention (PCI) procedure and is mostly done under the guidance of fluoroscope and transesophageal echocardiography (TEE). The minimum invasive surgery allows better patient compliance and faster recovery too.

The main current occluders for ASD and/or PFO closure are generally made of a metal frame (specifically made of Nitinol or Phynox) with synthetic fabrics (specifically made of polyester, Dacron or PTFE) or collagen matrix patches used as inserts. The metal frame usually has the form of an umbrella on each side of the opening combined by a metallic waist. The occluders are usually folded and inserted into a trans-luminal sheath, which is placed at the ASD/PFO location. Then the devices are deployed to seal the ASD/PFO under fluoroscopy and/or echocardiography.

After the ASD/PFO defect is closed by an occluder, a layer of ingrown tissue will usually cover the device and, will thus close the defect. Although elegant and smart device designs have been achieved owing to metal flexibility and excellent modulus, permanent presence of metal in the mammalian body leads to allergy and long-term toxicity risk. Metal-rich devices are also related to problems like friction lesions, perforations, erosion and thromboembolism. Furthermore, these devices made of metal and synthetic fabrics may obstruct the trans-septal access for the left atrium, which is of significant importance for the future treatment of left-sided heart disease including percutaneous heart valve repair or replacement, arrhythmia studies, and therapies (e.g., pulmonary vein exclusion and left atrial appendage closure).

Considering the above comments, it is therefore an object of the present invention to overcome at least some of the above-mentioned problems of existing occluders and to provide an alternative occlusion device for closing an opening in a tissue.

SUMMARY OF THE INVENTION

According to a first aspect of the present application, an occlusion device for closing an anatomical defect in tissue is provided consisting of an opening connecting a front side and a back side of a tissue. The occlusion device includes a scaffold comprising or consisting of:
  a proximal support structure comprising at least two arms;
  a distal support structure comprising at least two arms; and
  a waist portion adapted for extending through the opening of the defect and connecting the proximal support structure with the distal support structure
wherein the proximal support structure and the distal support structure are of a polymeric material.

According to a second aspect, an alternative occlusion device for closing an anatomical defect in tissue is provided, wherein the anatomical defect comprises an opening connecting a front side and a back side of a tissue. The occlusion device includes, but is not limited to, a scaffold comprising:
  a proximal support structure comprising at least two arms;
  a distal support structure comprising at least three arms and a distal occlusion film supported by at least two of these three arms; and
  a waist portion adapted for extending through the opening of the defect and connecting the proximal support structure with the distal support structure
wherein the proximal support structure and the distal support structure are of a polymeric material.

According to a third aspect, a method of closing an anatomical defect in a tissue is provided consisting of an opening connecting a front side and a back side of a tissue. The method comprises or consists of the steps:

providing a sheath into which an occlusion device according to the first aspect has been inserted, moving the occlusion device through the sheath to the site of the anatomical defect by using a delivering means, moving the proximal support structure of the occlusion device out of the sheath through the defect to the front side of the tissue, deploying the proximal support structure at the front side of the tissue to close the defect from the front side, withdrawing the sheath to release the waist portion of the occlusion device in the opening and the distal support portion and the waist portion of the occlusion device at the back side of the tissue, and deploying the distal support structure of the occlusion device at the anatomical defect to close the defect from the back side of the tissue.

Alternative embodiments as well as other aspects and features of the present invention are described in the dependent claims and will become apparent from the following description of specific embodiments and non-limiting examples of the present invention.

BRIEF DESCRIPTION OF THE DRAWINGS

The invention will be better understood with reference to the detailed description when considered in conjunction with the non-limiting examples and the accompanying drawings.

FIGS. 5a and b show mould sets used in the fabrication process of one embodiment described herein, wherein FIG. 5a shows a mould for the waist portion and FIG. 5b shows moulds for the proximal and the distal support structures and their respective films if present.

FIG. 6a shows the waist portion, FIG. 6b shows the proximal support structure and the proximal occlusion film during the manufacturing process being in a mold, FIG. 6c shows the combination of the waist portion and the proximal structural part while FIG. 6d shows a complete occlusion device as described above.

FIGS. 15 a and b show the stress relaxation of a copolymer candidate and several blends.

FIG. 34a shows the occlusion device inserted into a sheath which has been positioned at the tissue defect. In FIG. 34b, the sheath is pulled back to release the proximal support structure, wherein the proximal support structure deploys from its folded state into its working structure. FIG. 34c shows the step of pulling back the sheath of the catheter to anchor the proximal support structure at the front side of the tissue defect, generally the left atrium side of a PFO. FIG. 34d shows the step of further pulling back the catheter to release the folded distal support structure, while the distal support structure automatically recovers to its original shape. In FIG. 34e, the distal support structure is fully recovered to its original shape and seals the tissue opening from the back side, generally the right atrium side of a PFO. FIG. 34f shows the step of retrieving the delivering system after disconnecting it from the distal support structure to complete the deployment of the occlusion device.

DETAILED DESCRIPTION OF THE INVENTION

Figure 1:
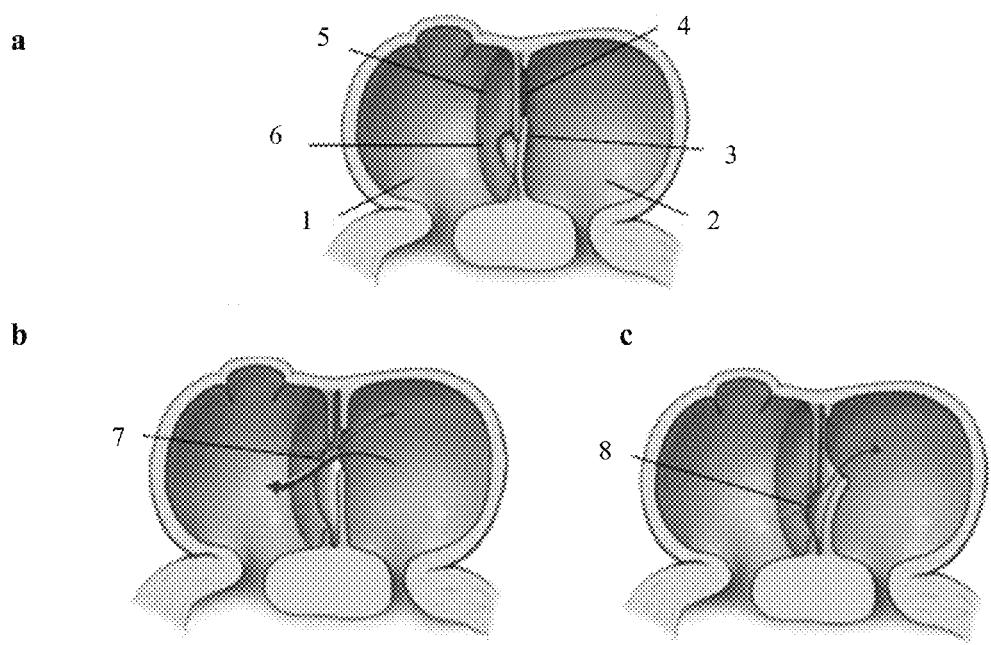
FIGS. 1a-c show (a) normal septa, (b) septa with an atrial septal defect (ASD) and (c) septa with patent foramen ovale (PFO).

According to a first aspect, the present invention refers to an occlusion device for closing an anatomical defect in tissue. In the context of the present invention, an occlusion device is a catheter-deliverable device that closes a hole in the wall of a tissue like a hole or opening in the septa of a heart. Once in place the occlusion device is released on both sides of the defect from the sheath and the deployed occlusion device will be kept in place by the deployed proximal support structure and the deployed distal support structure, respectively. The pressure of both support structures against both sides of the opening closes the opening from both sides. The occlusion device thus can function as a permanent implant that stays in the body after the procedure. The occlusion device can, however, also be used in in vitro methods for closing tissue defects outside the body, for example.

The occlusion device of the first aspect comprises a scaffold which can comprise a proximal support structure comprising at least two arms, a distal support structure comprising at least two arms, and a waist portion connecting the proximal support structure and the distal support structure.

The scaffold can further comprise occlusion films. In this embodiment, the arms of the proximal support structure and/or the distal support structure can support a proximal or a distal occlusion film.

The scaffold, that means one or more of the proximal support structure, the distal support structure, the waist portion, the proximal occlusion film and the distal occlusion film, can be made of a polymeric material. In an alternative embodiment of the first aspect, the entire occlusion device can be made of a polymeric material. The polymeric material can be a non-biodegradable or biodegradable polymer or copolymer.

In the context of the present invention, the term "non-biodegradable polymer" refers to a polymer material comprising one or more polymer components that cannot be removed from a localized area by metabolic processes. Various examples of non-biodegradable polymers can include, but are not limited to, polyurethane, poly(ether urethanes), poly(ester urethanes), polyvinylchloride, polyalkylenes, polyethylene terephthalate polyvinylacetate, poly ethylene-co-vinyl acetate or nylon.

In the context of the present invention the term "biodegradable polymer" refers to a polymer material comprising one or more polymer components that can be completely removed from a localized area by physiological metabolic processes such as resorption. A "biodegradable" compound can, when taken up by a cell, be broken down into components by cellular machinery such as lysosomes or by hydrolysis that the cells can either reuse or dispose of without significant toxic effect on the cells. Examples of biodegradation processes include enzymatic and non-enzymatic hydrolysis, oxidation and reduction. Suitable conditions for non-enzymatic hydrolysis, for example, include exposure of biodegradable material to water at a temperature and a pH of a lysosome (i.e. the intracellular organelle). The degradation fragments typically induce no or little organ or cell overload or pathological processes caused by such overload or other adverse effects in vivo.

Various examples of biodegradable polymer materials are known in the art, any of which are generally suitable for use in the occlusion device of the present invention. Examples of polymers that are considered to be biodegradable include aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, polycarbonates naturally-occurring biodegradable polymers such as chitosan, collagen, starch, and blends thereof. Examples of polyortho esters include a polylactide, a polyglycolide, a polycaprolactone, a polylactic acid, a biodegradable polyamide, a biodegradable aliphatic polyester, and/or copolymers thereof or with other biodegradable polymers such as those mentioned above. Illustrative examples of biodegradable polymers include, but are not limited to a polylactide, such as poly(L-lactide) (PLLA), a polycaprolactone (PCL), a copolymer of polycaprolactone (PCL) and polylactic acid (PLA), or a copolymer of poly (lactide) and poly(glycolide) (PLGA). More specific examples of copolymers which can be used in the present invention include copolymers of polycaprolactone (PCL) and polylactic acid (PLA) having an glycolide content of about 5-60%, 5-55%, 5-50%, 10-50%, 15-50%, or 20-50%, or approximately 20%, 25%, 30%, 35%, or 50%, or a copolymer of poly(lactide) and poly(glycolide) (PLGA) having an glycolide content of about 5-50%, 10-50%, 15-50%, or 20-50%, or approximately 20%, 25%, 30%, 35%, or 50%, based on the copolymer composition.

The proximal support structure or the distal support structure, or both support structures can independently from each other comprise three or more spokes outwardly extending from the middle of the proximal support structure as the at least two arms. The spokes can be connected at their inner ends with each other so that they are arranged like spokes in a wheel or an umbrella. Alternatively, the spokes can be connected to a middle section, for example a joint section. In both cases the support structure can be foldable and can, thus, be adapted to be folded at their inner ends of the arms to be insertable into a sheath. Thereby, the arms can be folded inwardly or outwardly, i.e. in the direction of the waist portion or away from the waist portion. As an alternative, a joint section can be integrally provided together with the arms or spokes of the support structure, but can then be folded. Therefore, in one embodiment this part of the support structure is adapted to resist high mechanical stress.

The number of arms is not limited as long as the support structure can close the defect. For example, the defect can be closed by pressing the tissue ends against each other by means of the arms of the support structure from both sides of the tissue. Alternatively, in case the support structure comprises an occlusion film, the number of arms can include 2 or more arms as long as the support structure can support a proximal or a distal occlusion film, respectively. In another embodiment comprising or not comprising occlusion films, the proximal and/or the distal support structures can include, but are not limited to 2 to 8 arms or spokes, such as 2, 3, 4, 5, 6, 7, or 8 arms or spokes. The number of spokes in the proximal support structure and in the distal support structure can be the same or different.

The form of the arms or spokes is generally like a rod having a rounded or any other cross section, such as square, rectangular, hexagonal, octagonal or triangular. Rounded means in the context of the present application, that the supporting means can have a circular cross section or an oval cross section. The edging of the arms or spokes can be rounded.

In another embodiment, the outwardly extending arms are spokes forming together with the respective occlusion film a disk-shaped occlusion structure. Disk-shaped means in the context of this application that the shape is like a circular disk, but can also be curved like a shell. Thus, the disc-shaped occlusion structure may be in any form between a disk and a half-shell. If the support structure and the occlusion film are in a half-shell, they look like an umbrella when connected to the longitudinal waist portion.

In this regard, the proximal occlusion film can, in the context of the present application, be connected to the proximal support structure, for, example, by welding the film on the support structure. As an alternative to the welding of the film, the film can be glued, laminated or sewed to the support structure. In general one or more films can be used as the proximal occlusion film. For example, two, three, or four films can be provided on the proximal support structure in a laminated structure.

In a particular embodiment of the first aspect, the proximal support structure can be formed together with the proximal occlusion film by hot pressing in one or two consecutive steps. In one step, the supporting means are formed of the same material as the film, but having a higher thickness. Thereby, an integrally formed proximal occlusion disc comprising the proximal support structure and the proximal occlusion film can be easily formed.

Analogously, the distal occlusion film, or the two, three or four films, can be connected to the distal support structure in the same manner as described above for the proximal support structure. For example, the film or the films can be welded, glued, laminated, or sewed to the distal support structure or both can be integrally formed, for example in one or two consecutive steps by hot pressing.

The proximal and the distal occlusion films are adapted to be disposed together with the proximal support structure and the distal support structure at the front side or the back side of the defect in the tissue, respectively. The films are supported by the respective support structure.

In a further embodiment, the proximal occlusion film can extend between the arms of the proximal support structure. Extend in the context of the present application means that the film extends from one arm to the proximate arm and can be spanned between the arms or spokes. Alternatively, the proximal occlusion film can be spanned over the supporting means of the proximal support structure, thereby forming the disk-shaped structure for closing the defect from the front side of the tissue.

Similar to the proximal occlusion film, the distal occlusion film can extend between the arms of the distal support structure or can be spanned between or over the arms of the distal support structure, thereby forming the disk-shaped structure for closing the defect from the back side of the tissue.

The size and the form of the film section can be freely adjusted depending on the size of the defect to be closed. In addition, the dimensions of the proximal portion of the occlusion device and the distal portions of the occlusion film can be adjusted so that the device can be placed in and pushed through a catheter sheath and has a working size (diameter) of the film portions in the working structure which is sufficient for closing the opening, for example in the septum. Such a transcatheter-closeable defect usually has a diameter of up to 40 mm. The diameters of the occlusion devices, i.e. the diameter of the proximal and the distal occlusion films can be about 70 mm, 60 mm, 50, mm, 40 mm, 30 mm, 20 mm, or can be provided in a size range of about 12-16 mm. In one example, the proximal occlusion film has a diameter of about 12 mm and the distal occlusion film has a diameter of about 16 mm. The diameter depends on the size of the defect to be sealed. The size of the films, i.e. the proximal disk-shaped structure and the distal disk-shaped structure, should be adapted such that a defect can sufficiently be closed. Sufficiently closed means in the context of the present invention that after insertion of the occlusion device into an opening, the liquid flow from the back side to the front side and the liquid flow from the front side to the back side of the closed opening can no longer be observed, for example by echocardiography or any other method used in the art to measure the liquid flow through an opening.

The thickness of the occlusion films (if present) of the occlusion device can be at least about 10, 20, 30, 40, 50, 60, 70, 80, 90, 100, 110, 120 µm but below 500, 450, 400, 350, 300, 250, 200, 190, 180, 170, 160, 150 µm as long as the material has a suitable flexibility to be folded into the sheath during the deployment procedure.

The proximal support structure and/or the distal support structure can comprise a connector adapted for connecting the respective support structure with the waist portion. The connector can, for example, be a joint protruding in the middle of the proximal and/or distal support structure in the direction of the waist portion.

In one embodiment, the waist portion can be a tube, such as a polymeric tube, like a stem adapted to receive the joint of the proximal support structure from its proximal end and to receive the joint of the distal support structure from its distal end. Thus, the proximal support structure and the distal support structure can be connected by joint connection to the waist portion, respectively. The joints of the support structures can be adapted to be inserted into the waist portion, such as being inserted into the tube with the end of the joint not connected to the arm or spoke.

The waist portion can be formed to extend through the opening of the defect and can, thus, be adapted to the tissue thickness at the opening or can be elastic enough to accommodate different opening thicknesses. The elasticity can be adjusted by common methods such as the material elasticity, the material thickness, the wall thickness of the tube, and the like. The waist portion can have a length of between about 1 and 10 mm, for example, about 1, 2, 3, 4, 5, 6, 7, 8, 9, or 10 mm. The waist portion can be a tube having a diameter of about 0.5 to 2.0 mm, for example, about 0.5, 0.6, 0.7, 0.8, 0.9, 1.0, 1.1, 1.2, 1.3, 1.4, 1.5, 1.6, 1.7, 1.8, 1.9, or 2.0 mm. The wall thickness of the tube, if the waist portion is in the form of a tube, can be between about 0.05 and 0.50 mm, for example, about 0.05, 0.06, 0.07, 0.09; 0.11, 0.13, 0.15, 0.17, 0.19, 0.21, 0.23, 0.25, 0.27, 0.29, 0.30, 0.35, 0.40, 0.45 or 0.50 mm.

In alternative embodiments of this aspect, the waist portion can be a solid stem which is glued, welded or connected in a similar manner at the respective support structure.

In the occlusion device of the first aspect, it can be suitable to prepare separate parts of the device from different polymeric materials to specifically adjust the required performance of the material. For instance, the waist portion of the occlusion device can be made stiffer or more rigid than the proximal or distal support structures or the occlusion films. Otherwise, it is also possible to form all parts of the device from the same material but having specific thicknesses such that each part has the flexibility of stiffness required for its function. For example, in one embodiment the support structures or the waist portion can be stiffer than the film portions of the device. Using different polymeric materials can also serve to alter the biodegradability of different portions of the occlusion device to result in a sequential degradation of different parts of the occlusion device. For example, the material used for the waist portion can be manufactured of a polymeric material which degrades slower than the material used for the proximal and distal support structure. This could result in a closure of the defect without risking a further passage of body fluid from one side of the defect to the other.

In one embodiment, the stiffness of the proximal support structure is higher than the stiffness of the distal support structure. This can, for example be achieved by using different materials or by using different thicknesses of the support structures. If the material is different, the polymeric material of the proximal support structure can have a higher Young modulus than the polymeric material of the distal support structure. Due to this difference in Young modulus, the stiffness of each of the support structures can be adjusted such that during the use of the occlusion device the practitioner can check whether or not the device has been anchored at the front side of the defect or not.

The polymeric material of the proximal support structure can, for example, have a modulus range of about $10^7$ to about $10^9$ Pa at 37° C., more particularly between about $2\times10^7$ to about $10^9$ Pa, between about $5\times10^7$ to about $5\times10^8$ Pa, or about $2\times10^8$ Pa. The polymeric material of the distal support structure can, for example, have a modulus range of about $10^5$ to about $10^7$ Pa at 37° C., more particularly between about $10^5$ to about $5\times10^7$ Pa, between about $2\times10^5$ to about $2\times10^6$ Pa, or about $10^6$ Pa.

In one embodiment of the occlusion device of the first aspect, the entire occlusion device can be made of a polymeric material, like a biodegradable polymer to provide a fully bio-degradable occlusion device. That means that the materials of the above described scaffold and film section can be made of a bio-degradable material, particularly of bio-degradable polymers. In this embodiment, the material of the device can be fully biocompatible and can, for example, be absorbed by the body within short time of a few years to several months, such as 24, 20, 18, 16, 14, 12, 10, 9, 8, 7, 6, 5, 4, 3 or 2 months.

Approved by US FDA for other vascular applications, biodegradable polyesters are the most commonly used and promising bio-degradable materials of choice for blood contacting implants. They are biocompatible and can be tailored to degrade within a wide range of time frames. However, the loading and deployment of the occlusion devices usually involve drastic deformation and the polymers behave differently in terms of mechanical properties (e.g., much lower modulus, stress relaxation, and the like) compared with metals. In order to completely replace metal in the occluder design, the polymers are selected according to their mechanical behaviors. Meanwhile design should be taken out in a way to make full advantage of the material properties. Therefore, the film section of the occlusion device can generally be made of any biodegradable polymer having sufficient physical and mechanical properties for being spanned over or between the support structures of the occlusion device of the first aspect. Such a polymeric base material can include, but are not limited to, polycaprolactone (PCL), polylactic acid (PLA), polycaprolactone-co-lactide copolymer (PCL-PLA copolymer), polyglycolide (PGA), poly-L-lactide (PLLA), poly-D-lactide (PDLA), polylactide-co-glycolide copolymer (PLGA), polylactic acid-polyethylene oxide copolymers, polygluconate, polyhydroxybutyrate, polyanhydride, polyphosphoester, poly(amino acids), polydioxanone, cellulose, collagen, chitosan or copolymers thereof.

Most bioabsorbable polymers available today, namely polylatic acids (PLA), polycaprolactone (PCL) and polylactic-co-glycolic acid (PLGA) however display a very similar mechanical behavior, with a high Young's modulus and rather low elongation at break values. Sometimes these polymers seem in a pure form inappropriate for this clinical application where highly flexible biodegradable materials are required because of the huge expansion ratio before and after deployment. One of the most practical strategies for tuning the properties of polymers is blending with another polymer or copolymerization. Copolymerization facilitates a broad range of properties, including good mechanical strength, biocompatibility, biodegradability, and processability, which makes them excellent materials for medical application. PCL is for example a good candidate to toughen PLA which may increase the flexibility of PLA chain. The random copolymer of PCL and PLA (PCL-co-PLA) degrades faster than either homo-polymers. The rate of degradation increases with the increase of PLA content in the copolymer. The fastest degradation rate is obtained when PLA-PCL is about 70:30, but the degradation rate is still within an suitable range within PLA:PCL of about 90:10-50:50, more particular of about 80:20-60:40. Furthermore, PLA-PCL copolymer has good mechanical and biocompatible properties.

A list of exemplary candidate polymers is shown in the following Table 1. The respective glass transition temperature (Tg) and melting temperature (Tm) have been determined by differential scanning calorimetry (DSC).

TABLE 1

Bio-degradable polymers and their thermal properties

| Materials | Tg (° C.) | Tm (° C.) |
|---|---|---|
| PLA IV2.38 (Purac) | 60 | 175 |
| PLGA 80/20 IV1.7-2.6 (Purac) | 52 | 120 |
| PCL Mw 80K (Aldrich) | −60 | 62 |
| PLA-PCL Copolymer 70/30 IV1.62 (Purac) | 15 | 112 |

In case pure PLA is too stiff, it can be blended into the PLA-PCL copolymer at certain ratios to adjust the Young's modulus within about $1 \times 10^4$ to about $1 \times 10^7$ Pa at 37° C., more particularly more than about $1 \times 10^4$, $2 \times 10^4$, $3 \times 10^4$, $4 \times 10^4$, $5 \times 10^4$ and less than about $1 \times 10^7$, $5 \times 10^6$, $1 \times 10^6$, $5 \times 10^5$, $1 \times 10^5$. If the modulus is too low and a higher modulus is desired, blends with other monomers or filler occlusion (such as, e.g., metal oxides, metal salts such as sulfates, chlorides or the like, organic fillers etc.) are useful, although the degree of stress relaxation is greater than in the pure PLA-PCL copolymer. For certain circumstances such as the films or the spokes where low stiffness and high flexibility are required, the pure copolymer can be a good option. Therefore, the physical parameters of the polymeric material can be adjusted to the specific use of the occluder part by general methods outlined above. The skilled person knows mechanical tests for testing the stress relaxation of the respective polymeric materials as it is, for example, shown in FIGS. 14 and 15 and described in Example 5.

For adjusting the performance of the polymers, plasticizers could be used. In the context of the present invention, "plasticizer" generally means a substance added to a polymer material to soften it and to improve flexibility. More particularly, the plasticizer which can be used in the occlusion device of the present invention can preferably lower the glass transition temperature, Tg, the modulus, i.e. increases the elongation at break, or changes the crystalline behavior of a polymer material or can adjust the melting temperature, Tm. Any known plasticizer can be used in the polymeric material as long as the plasticizer provides the polymer with the above-mentioned properties. The plasticizer may also be biocompatible, especially non-toxic. However, due to the small amount of plasticizer used compared to the entire body mass of a patient, use of a plasticizer that may have some adverse effects on the human body is also within the scope of the invention. Some illustrative examples of plasticizer that can be used in the present invention include, but are not limited to triethyl citrate (TEC), polyalkylene glycols such as polyethylene glycols (PEG) or polypropylene glycols, propylene glycol (PG) glycerol, di-2-ethylhexyladipate (dioctyladipate), di-2-ethylhexylphthalate (dioctylphthalate), dicyclohexylphthalate; diisononyladipate; diisononylphthlate; n-butyl benzyl phthalate, 1,3-butylene glycol/adipic acid polyester (1700-2200 MW) containing 16 weight percent terminal myristic, palmitic and stearic acid ester functionality. Other examples of plasticizers include epoxidized butyl esters of linseed oil fatty acid, epoxidized linseed oil or epoxidized soya oil. Examples of polyalkylene glycols include low molecular weight (MW) compounds having an MW of about 60-about 8000, or about 100-6000, about 100-5000, about 100-4000, or about 150-2000. Illustrative examples include diethylene glycol, triethylene glycol, dipropylene glycol, or tripropylene glycol, too name only a few.

The amount of plasticizer is not limited but is generally adjusted such that the biodegradable polymer material maintains mechanical integrity during its use, including for example, during the storage and upon deployment. In some embodiments of the invention, the plasticizer can be contained in one or all of the polymer materials in an amount of about 1-about 30 wt %, or about 1-25 wt %, about 2-25 wt %, about 3-25 wt %, about 4-25 wt %, about 5-25 wt %, about 6-25 wt %, about 2-20 wt %, about 3-20 wt %, about 4-20 wt %, or about 5-20 wt %, based on the dry weight of the polymer material. In line with the above, the amount of plasticizers can for example be about 1, 2, 3, 4, 5, 6, 7, 8, 9, 10, 12, 15, 17, 19, 21, 23, 25, 27, or 29 wt %, based on dry weight of the respective polymer material.

In an alternative embodiment of the occlusion device of the first aspect, one or more elements selected from the proximal support structure, the proximal occlusion film, the distal support structure, the distal occlusion film, and the waist portion can be made of a material comprising a therapeutically active agent.

In the context of the present invention, the term "therapeutically active agent" generally means a therapeutic or pharmaceutical agent which can be mixed into the polymer composition, or impregnated or incorporated into the tube and wire structures to provide drug-containing tubes or wires. The therapeutic agent can be any therapeutic or pharmaceutical agent suitable for use in drug-containing materials for occlusion devices. Various examples include, but are not limited to antiproliferative/antimitotic agents including natural products, such as vinca alkaloids (e.g. vinblastine, vincristine, and vinorelbine), paclitaxel, epipodophyllotoxins (e.g. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiproliferative/antimitotic alkylating agents such as nitrogen mustards (such as mechlorethamine, cyclophosphamide and analogs, melphalan, chlorambucil), ethylenimines and methylmelamines (hexamethylmelamine and thiotepa), alkyl sulfonates-busulfan, nirosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine{cladribine}); platinum coordination, complexes (cisplatin, carboplatin), procarbazine, hydroxyurea, mitotane, aminoglutethimide; hormones (e.g. estrogen); anticoagulants (heparin, synthetic heparin salts and other inhibitors of thrombin); fibrinolytic agents (such as tissue plasminogen activator, streptokinase and urokinase); antiplatelet (such as aspirin, dipyridamole, ticlopidine, clopidogrel, abciximab); antimigratory; antisecretory (such as breveldin); antiinflammatory: such as adrenocortical steroids (cortisol, cortisone, fludrocortisone, prednisone, prednisolone, 6-alpha-methylprednisolone, triamcinolone, betamethasone, and dexamethasone), non-steroidal agents (such as salicylic acid derivatives e.g. aspirin); para-aminophenol derivatives (e.g. acetaminophen); indole and indene acetic acids (such as indomethacin, sulindac, and etodalac), heteroaryl acetic acids (such as tolmetin, diclofenac, and ketorolac), arylpropionic acids (such as ibuprofen and derivatives), anthranilic acids (such as mefenamic acid, and meclofenamic acid), enolic acids (such as piroxicam, tenoxicam, phenylbutazone, and oxyphenthatrazone), nabumetone, gold compounds (such as auranofin, aurothioglucose, gold sodium thiomalate); immunosuppressive (such as cyclosporine, tacrolimus (FK-506), sirolimus (rapamycin), azathioprine, mycophenolate mofetil); angiogenic such as vascular endothelial growth factor (VEGF), fibroblast growth factor (FGF); nitric oxide donors; anti-sense oligo nucleotides and combinations thereof.

The therapeutic agent can particularly include, but is not limited to, a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, or an anti-hypertensive agent to improve the sealing effect, the healing process, or preventing thrombi, for example. Heparin is well known for anticoagulation and has been used to prevent clotting in many cardiovascular applications. In an alternative embodiment, for example, heparin can be included as an anti-clotting factor, for example by blending or impregnating it into the surface, of the polymeric material to provide a better blood biocompatibility.

In some embodiments of the invention, the anti-thrombotic drug can, for example, include, but are not limited to, small organic molecules such as clopidogrel, triflusal, or analog salicylic acid derivatives or a protein such as hirudine or thrombin. Illustrative examples of an anti-restenotic drug are sirolimus, also called rapamycin paclitaxel, and evolimus.

Another example of a therapeutic agent that may be used in the polymeric material is the compound known as elarofiban (b-[[[(3R)-1-[1-oxo-3-(4-piperidinyl)propyl]-3-piperidinyl] carbonyl]amino]-3-pyridinepropanoic acid, (bS)-(9CI), RWJ-53308) and elarofiban analogs that are described in International patent application WO2005/087266.

In this context, it is noted that the drug (therapeutically active agent) to be incorporated into one or more polymeric materials of the occlusion device can be a small organic molecule, a protein or a fragment of the protein, a peptide or a nucleic acid such as DNA or RNA. The term "small organic molecule" as used herein typically denotes an organic molecule comprising at least two carbon atoms, but preferably not more than 7 or 12 rotatable carbon bonds, having a molecular weight in the range between 100 and 2000 Dalton, or between 100 and 1000 Dalton, that optionally can include one or two metal atoms. The term "peptide" as used herein typically refers to a dipeptide or an oligopeptide with 2-about 40, 2-about 30, 2-about 20, 2-about 15, or 2-about 10 amino acid residues. The peptide may be a naturally occurring or synthetic peptide and may comprise—besides the 20 naturally occurring L-amino acids—D-amino acids, non-naturally occurring amino acids and/or amino acid analogs. With "protein" is meant any naturally occurring polypeptide that comprises more than 40 amino acid residues. The protein can be a full length protein or a truncated form, for example, an active fragment. Illustrative examples of proteins include, but are not limited to antibodies or other binding proteins with antibody like properties (for example, affibodies or lipocalin muteins knows as Anticalins®) for selected cell receptors, growth factors such as VEGF (Vascular Endothelial Growth Factor) and similar factors for transmitting signals, cardiovascular therapeutic proteins or cardiac hormones and active fragments thereof or prohormones or preprohormones of such cardiac hormones (these hormones or the prohormones can either be peptides as defined herein, if they have less than 40 amino acid residues of a protein, should there polypeptide sequence contain more the 40 amino acid residues). Further examples for cardiovascular therapeutic agents can be peptides or DNA such as the DNA for nitric oxide. Examples of nucleic acid molecules include sense or anti-sense DNA molecules (if expression of a target gene is to be controlled) or the coding sequence (either alone or in gene-therapy vector, for example) of a therapeutically active protein that is to be produced. In such a case, the nucleic acid may code for a protein that promotes wound healing as described in International patent application WO 97/47254, for example.

All therapeutically active agents mentioned above can be used alone or in any combination thereof in the polymer material of this embodiment of the invention. If a therapeutically active is contained, the agent can be incorporated into the polymer material by admixing, impregnating, or the like, wherein the drug does not necessarily need to be uniformly distributed within the polymer material.

The amount of the therapeutically active agent (or 2 or more agents together) in the polymeric material is not limited and can be as high as wanted as long as the physical properties of the polymer material, especially the glass transition temperature and the melting temperature, are not adversely affected. In some embodiments, the amount of the therapeutically active agent, based on the dry weight of the polymer material that contains the agent, may be up to about 35 wt %. The therapeutically active agent may be present in an amount of 0.1 to 35 wt %, 1 to 35 wt % or 1 to 10, 15, 20, 25 or 30 wt % based on the dry weight of the polymer material that contains the drug. In this context, it is again noted that it is possible to include more than one therapeutically active agent of the same or different type into a polymer material of the films or the wires, for example, an anti-restenotic drug and an anti-inflammatory drug or two anti-thrombotic drugs.

In a further embodiment of the occlusion device one or more elements selected from the group of the proximal support structure, the distal support structure, the waist portion, the proximal occlusion film, or the distal occlusion film can comprise a radiopacifier deposited at its surface and/or blended in the material the elements comprise. For example, the radiopacifier can be present in the proximal and distal support structures and the waist portion of the occlusion device.

The radiopacifier can for example be a material including metals, metal oxides or metal salts, such as gold particles, bariums salts or bismuth glasses, for example, but are not limited to these examples. In the present embodiment, $BaSO_4$ can be used for radio-opacity. In the films, the radiopacifier can be incorporated into the polymeric material by solution casting in an amount of more than 0.1, 0.2, 0.3, 0.4, 0.5, 1.0, 1.5, 2.0, 2.5, 3.0, 3.5, 4.0% (w/w) to less than 50, 45, 40, 35, 30, 25, 20, 15, 10, 9, 8, 7, 6, 5% (w/w) as long as the films are provided with radio-opacity for making the device visible by means of fluoroscopy, for example, during the deployment procedure. In the films, the radiopacifier can often be less concentrated compared to the support structures to avoid any affecting of the physical properties of the polymers or copolymers. In other parts of the occlusion device, for example in the waist portion or the proximal or distal support structures, the amount of radiopacifier can be increased, because a higher stiffness of the waist portion or the support structures is suitable and the visibility of the occlusion device can simultaneously be improved. For example, the films of the occlusion device can be solution casted or hot-pressed with about 4% (w/w) $BaSO_4$. The $BaSO_4$ also enhances stiffness and non-stickiness. The waist portion can, for example, be made of a copolymer with about 40% (w/w) $BaSO_4$ for providing good radio-opacity. The same can apply for the proximal and the distal support structures.

In another embodiment of the first aspect, the occlusion device additionally comprises a delivering system. In the context of the application, the term "delivering system" means a system which is suitable to deliver the occlusion device to the desired place in the body of a subject, like a mammal (including, e.g., primates including humans, rodents such as mice and rats, and ungulates such as pigs and the like) to be treated. The delivering system, however, does usually not be part of the device maintaining in the body of a patient, but can be removed at the end of the deployment procedure of the occlusion device.

The delivering system can comprise a sheath and at least one first delivering means adapted to move the occlusion device through a sheath for loading it into the sheath. The at least first delivering wire can be removably connected to the proximal support structure or the distal support structure.

Removably connected means that it can be removed from the occlusion device after the occlusion device has been positioned. The at least first delivering means can move the occlusion device through the sheath for example, by pulling it at the proximal end or by pushing it at the distal end.

The at least one first delivering means can be a loading wire removably connected to the proximal support structure. To be removably connected, the loading wire can form a loop running through the proximal support structure. If the loading wire is in loop form, it can be adapted to be removed from the proximal support structure, for example, by pulling at one end of the loading wire.

The loading wire can be made of any surgical suture such as non-absorbable or absorbable sutures. Absorbable sutures are made of materials which are broken down in tissue after a given period of time, which depending on the material can be from ten days to eight weeks. They are generally used therefore in many of the internal tissues of the body. Absorbable sutures were originally made of the intestines of sheep, the so called catgut. The majority of absorbable sutures are made of synthetic polymer fibers, which may be braided or monofilament. Exemplary polymeric materials of such synthetic absorbable sutures are various blends of polyglycolic acid, polylactic acid or caprolactone. Non-absorbable sutures are generally made of materials which are not metabolized by the body, and are used therefore either on skin wound closure, where the sutures can be removed after a few weeks, or in some inner tissues in which absorbable sutures are not adequate. This is the case, for example, in the heart and in blood vessels, whose rhythmic movement requires a suture which stays longer than three weeks, to give the wound enough time to close. Other organs, like the bladder, contain fluids which make absorbable sutures disappear in only a few days, too early for the wound to heal. There are several materials used for non-absorbable sutures. The most common is a natural fiber, silk, which undergoes a special manufacturing process to make it adequate for its use in surgery. Other non-absorbable sutures are made of artificial fibers, like polypropylene, polyester or nylon; these may or may not have coatings to enhance their performance characteristics.

Since the loading wire does generally not come into contact with the body and is usually completely removed after insertion of the occlusion device into the sheath of a catheter, the loading wire can be any surgical suture as described above and does not necessarily be bio-absorbable. Therefore; in one embodiment of the first aspect, polymeric wires such as nylon sutures can be used. The diameter of the loading wire can be between 0.2 and 0.5, between 0.25 and 0.45, between 0.3 and 0.4 mm, for example 0.36 mm (e.g. a Nylon wire like PDS II 4/0 suture).

The occlusion device of the above aspect can further comprise a guide tube adapted to house the loading wire and to guide the loading wire through the sheath. The guide tube can be made of a polymeric material which is not hazardous for the patient. However, any other of the afore-mentioned non-biodegradable or biodegradable polymer materials could be used for the guide tube. The material of the guide tube can be any material if it is flexible enough to be inserted into a sheath of a catheter. The tube can be a polymeric tube, usually made of a bisostable polymer, such as a PTFE tube having an outer diameter of about 1.0-2.0 mm, 1.2-1.9 mm, 1.4-1.8 mm, 1.6-1.7 mm, for example about 1.65 mm, and an inner diameter of about 0.5-1.5 mm, 0.7-1.3 mm, 0.9-1.1 mm, for example about 1.0 mm.

The occlusion device can further comprise a second delivering means. This second delivering means can, for example, be a deployment tube adapted to push the occlusion device with the distal support structure through the sheath. The material of the deployment tube can be of any material if it is flexible enough to be inserted into a sheath of a catheter. Similar to the above guide tube, however, the deployment tube can be made of a polymeric material which is not hazardous for the patient. However, any other of the afore-mentioned non-biodegradable or biodegradable polymer materials could be used for the deployment tube. The tube can be a polymeric tube, usually made of a biostable polymer, such as a PTFE tube of an outer diameter of about 1.5-3.5 mm, 1.8-3.2 mm, 2.1-2.9 mm, 2.3-2.7 mm, for example about 2.5 mm, and an inner diameter of about 0.5-1.5 mm, 0.7-1.3 mm, 0.9-1.1 mm, for example about 1.0 mm.

In a further embodiment of the above aspect, the delivering system of the occlusion device can further comprise a retrieval wire removably connected to the distal support structure. The retrieval wire can form a loop running through the distal support structure to be removably connected to the distal support structure. If the retrieval wire is in loop form, it can be adapted to be removed from the distal support structure, for example, by pulling at one end of the retrieval wire. Since the retrieval wire is usually completely removed after deploying the occlusion device at the defect, the retrieval wire can be made of any surgical suture as described above for the loading wire and does not necessarily be bio-absorbable. Therefore, in one embodiment of the first aspect, polymeric wires such as nylon sutures can be used. The diameter of the retrieval wire can be between 0.2 and 0.5, between 0.25 and 0.45, between 0.3 and 0.4 mm, for example 0.36 mm (e.g. a Nylon wire like PDS II 4/0 suture). The retrieval wire can be housed in the deployment tube to prevent that the wires are entangled during the deployment procedure of the occlusion device.

The occlusion device of the first aspect can further comprise as an additional means of the delivering system a sheath adapted to include at least the occlusion device including the at least one first delivering means and the optionally provided retrieval wire and second delivering means.

The above described occlusion device of the first aspect including the above described delivering system can be preloaded in a sheath or can be prepared for preloading the occlusion device and the delivering system shortly before the deployment procedure is applied. Generally, the occlusion device is provided in a package which can then be sterilized. The sterilization can be carried out by any conventional process as long as the package with the occlusion device is sufficiently sterilized. An example of such conventional sterilization processes is ethylene oxide (ETO) sterilization in a standard ETO sterilization pouch. The occlusion device with or without the delivering system can be sealed in a package and then over at least 6 hours purged with ETO at about 37° C., usually followed by additional ETO purging of ETO gas at ambient temperatures. The additional purging step can be 5 hours or more, such as 6, 7, 8, 9, 10, 12, 14, 16, 18, 20, 22, 24 hours, especially about 16 hours. Therefore, in one embodiment of the first aspect, the occlusion device is provided in a sterilized package.

According to a second aspect, the present invention refers to an alternative occlusion device for closing an anatomical defect in tissue. According to the present application, the occlusion device of the second aspect is similar to the occlusion device of the first aspect and, thus, all definitions and explanations made with respect to the first aspect are the same in the second aspect. In order to avoid the repetition of such parts which are identical, only the differences to the first aspect are described in the following in greater detail. That means the occlusion device of the second aspect usually can have the same parts, members, materials, additional functional features and/or optional embodiments as the occlusion device of the first aspect. It is needless to say that all embodiments exemplified for the first aspect could be applied to the occlusion device of the second aspect in the same manner and in any combination as in the occlusion device of the first aspect.

The occlusion device of the second aspect comprises a scaffold which can comprise a proximal support structure comprising at least two arms, a distal support structure comprising at least three arms and a distal occlusion film supported by at least two of these three arms, and a waist portion connecting the proximal support structure and the distal support structure.

In this embodiment, the arms of the proximal support structure and/or the distal support structure can support a proximal or a distal occlusion film. In case the support structure has three or more arms, the film can extend between two of these arms or can be spanned over two, three, four, or more arms of the support structure.

The scaffold of the occlusion device according to the second aspect can further comprise reinforcing means. For the reinforcing means any means suitable to strengthen the stability of the proximal support structure can be used. The reinforcing means additionally help to strengthening the anchoring function of the at least two arms at the proximal side of the defect. According to an embodiment, the reinforcing means are reinforcing films extending from the end of the waist portion which is connected to the distal support structure to the proximal occlusion film supported by the arms of the proximal support structure. The reinforcing films can be connected, e.g. bonded, glued, welded, or sewed, to the proximal occlusion film at a position between the center of the proximal support structure and the middle of one of the arms, respectively. In one embodiment, all arms, that means at least two of the arms of the proximal support structure are reinforced by the reinforcing means. In another embodiment, the distance between the two reinforced films cannot be larger than the maximum diameter of the defect to be closed. If the distance is shorter or equal to the maximum diameter of the defect, the waist portion and the reinforcing means will be fit well within the tissue defect, e.g. the atrial hole of the ASD or PFO defect.

The scaffold, that means one or more of the proximal support structure, the distal support structure, the waist portion, the proximal occlusion film and the optional distal occlusion film, can be made of a polymeric material. In an alternative embodiment of the second aspect, the entire occlusion device can be made of a polymeric material. The polymeric material can, analogously as in the occlusion device of the first aspect, be a non-biodegradable or biodegradable polymer or copolymer. The same polymer materials as defined for the materials of the first aspect can be used.

The proximal support structure can comprise two or more spokes outwardly extending from the middle of the proximal support structure as the at least two arms. The spokes can be connected at their inner ends with each other so that they are arranged like spokes in a wheel. Alternatively, the spokes can be connected to a middle section, for example a joint section. In both cases the support structure can be foldable and can, thus, be adapted to be folded at their inner ends of the arms to be insertable into a sheath. Thereby, the arms can be folded inwardly or outwardly, i.e. in the direction of the waist portion or away from the waist portion. In case reinforcing members are provided at the proximal support structure, the arms are foldable inwardly in the direction of the waist portion, wherein the reinforcing members can be folded simultaneously. As an alternative, a joint section can be integrally provided together with the arms or spokes of the support structure. The arms are provided in such a manner that they can be folded inwardly or outwardly at the position where they are connected to the joint section. Therefore, in one embodiment this part of the support structure is adapted to resist high mechanical stress.

The distal support structure can comprise three, four, five, six, or more spokes outwardly extending from a middle section in the middle of the proximal support structure as the at least three arms and are connected at their inner end with each other. The spokes can be connected at their inner ends to a middle section, for example a joint section. The support structure can be foldable and can, thus, be adapted to be folded at their inner ends of the arms to be insertable into a sheath. Thereby, the arms can be folded inwardly or outwardly, i.e. in the direction of the waist portion or away from the waist portion. As an alternative, a joint section can be integrally provided together with the arms or spokes of the support structure. The arms are provided in such a manner that they can be folded inwardly or outwardly at the position where they are connected to the joint section. Therefore, in one embodiment this part of the support structure is adapted to resist high mechanical stress.

The number of arms is not limited as long as the support structure can close the defect. For example, if the tissue defect is a PFO (as shown in FIG. 1c), the defect can be closed by pressing the overlaying tissue ends of a PFO defect against each other by means of the arms of the support structures from both sides of the tissue. Alternatively, if the defect is for example an ASD (as shown in FIG. 1b), the support structure can comprise an occlusion film. In this case, the number of arms can include 2 or more arms in the proximal support structure or 4 or more arms or spokes in the distal support structure as long as the support structure can support a proximal or a distal occlusion film, respectively.

In another embodiment comprising or not comprising occlusion films, the distal support structure can include, but is not limited to a support structure with 3 to 8 arms or spokes, such as 3, 4, 5, 6, 7, or 8 arms or spokes. The number of spokes in the proximal support structure can include, but is not limited to 2 to 8 arms or spokes, such as 3, 4, 5, 6, 7, or 8 arms or spokes and can be the same or different as in the distal support structure. The use of more than 3 arms, e.g. 4 arms, can assist in fast unfolding of the distal occlusion film into its expanded working structure after the distal support structure is deployed out of the sheath. Unfolding of the distal support structure can further supported by using a shape-memory material for the arms to facilitate the recovering into its original shape after deployment.

The form of the arms or spokes is generally like a rod and can have the same form as in the occlusion device of the first aspect. The occlusion films can be provided in the same manner as was described in the first aspect.

Figure 29:
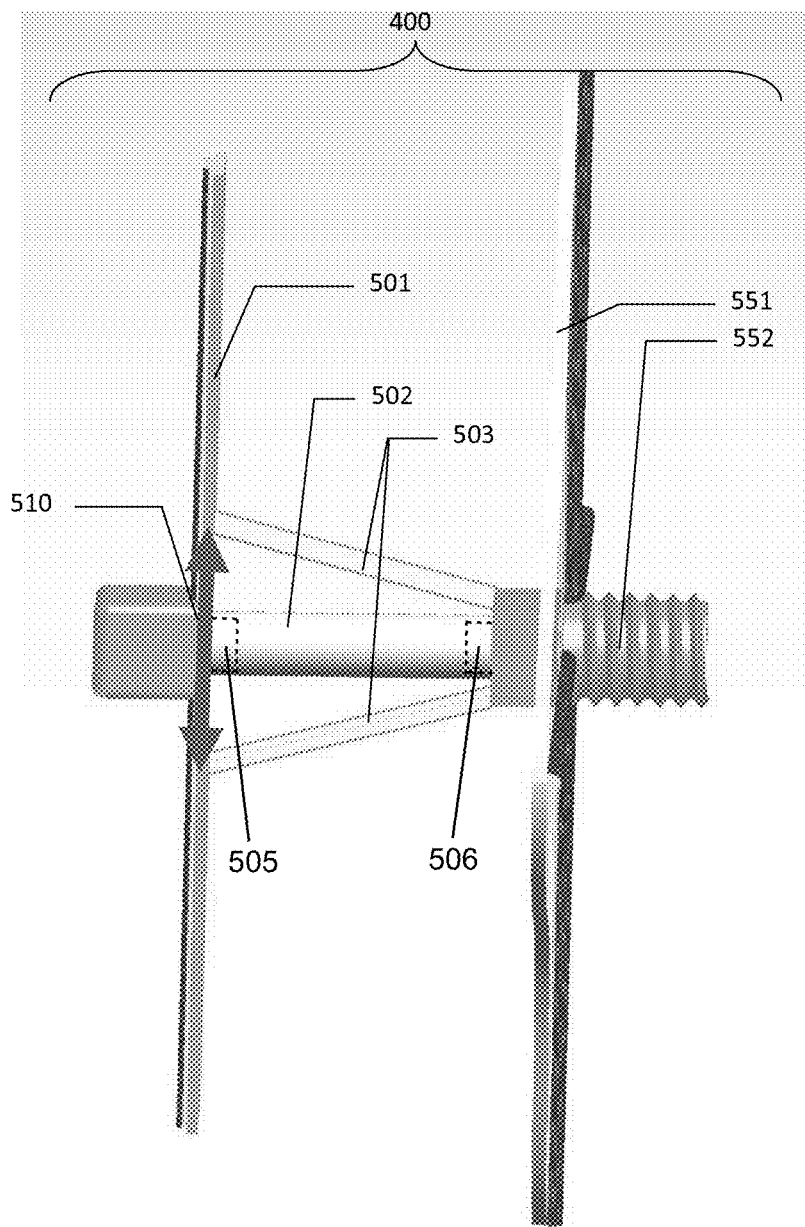
FIG. 29 shows a perspective view of the occlusion device shown in FIG. 28 in its assembled state.

In a further embodiment, the occlusion device of the second aspect includes proximal and/or distal support structures (501, 551) and a connector (505, 506) adapted for connecting the respective support structure with the waist portion (502), as shown in FIG. 29. In one embodiment, the waist portion (502) comprises a hollow tube, which can be a flexible hollow tube. In this context 'flexible' means that the form of the tube can be changed to a suitable amount, for example by bending or stretching. In the embodiment having a flexible hollow tube as the waist portion (502), the proximal and/or the distal support structure (501, 551) can be connected via a respective connector (505, 506), such as a hollow joint protruding in the middle of the proximal and/or distal support structure in the direction of the waist portion (502). The joint-like connectors (505, 506) are adapted to be insertable into the hollow tube of the waist portion (502) either from the distal or the proximal end of the hollow tube. In this embodiment, the connection can be fitted by a quick-fit connection, a screw connection, or any other connection. In addition, the connection could be strengthened by using a bonding or gluing agent, or by welding the parts together.

The waist portion can be formed to extend through the opening of the defect and can, therefore be adapted to the tissue thickness at the opening or can be elastic enough to accommodate different opening thicknesses. The elasticity can be adjusted by common methods such as the material elasticity, the material thickness, the wall thickness of the tube, and the like. The waist portion can have a length of between about 1 and 10 mm, for example, about 1, 2, 3, 4, 5, 6, 7, 8, 9, or 10 mm. The waist portion can be a tube having a diameter of about 0.5 to 2.0 mm, for example, about 0.5, 0.6, 0.7, 0.8, 0.9, 1.0, 1.1, 1.2, 1.3, 1.4, 1.5, 1.6, 1.7, 1.8, 1.9, or 2.0 mm. The wall thickness of the tube, if the waist portion is in the form of a tube, can be between about 0.05 and 0.50 mm, for example, about 0.05, 0.06, 0.07, 0.09, 0.11, 0.13, 0.15, 0.17, 0.19, 0.21, 0.23, 0.25, 0.27, 0.29, 0.30, 0.35, 0.40, 0.45 or 0.50 mm. The diameters and the wall thickness of the connectors of the proximal and distal support structures are adapted to the inner diameter of the waist portion so that they fit to the waist portion. The length and the wall thickness of the connectors are adapted such that the total length of both joints of the connectors is not larger than the length of the waist portion, but long enough to be connected with the waist portion such that the connection does not be disconnected during operation.

In one embodiment of the occlusion device according to the second aspect, the occlusion device further comprises a delivering system. Similar as in the first aspect, the delivering system does usually not form part of the occlusion device which remains at the defect side in the body of the patient, but can be removed at the end of the deployment procedure of the occlusion device.

The delivering system can comprise at least one first delivering means adapted to move the occlusion device through a sheath, and a sheath. In one embodiment, the first delivering means can be a rod removably connected to the proximal support structure. Removably connected in the context of the invention means that it can, be connected to the proximal support structure for loading the occlusion device into the sheath and for deploying it at the tissue defect side, for example in the body of a patient, but it can be removed from the occlusion device after the occlusion device has been correctly positioned. The first delivering means can move the occlusion device or the proximal support structure of the occlusion device through the sheath or out of the sheath. Movement of the device can be accomplished, for example, by pulling or pushing it at the proximal end. If the first delivering means is engaged at the proximal end of the occlusion device, it runs through the hollow tube in the middle section of the distal support structure and the hollow tube of the waist portion.

In one embodiment of the first delivering means, the means can be a rod which can be removably connected to the middle section of the proximal support structure. The rod can, for example, be engaged by means of a quick-fit mechanism or by a screwing mechanism.

The sheath can be a hollow polymeric tube adapted to house the folded occlusion device and the first delivering means. The sheath can be inserted into a catheter for delivering the occlusion device to the tissue defect of the patient.

In another embodiment, the delivering system comprises a second delivering means removably connected to the distal support structure and adapted to move the occlusion device through the sheath or to move it back into the sheath. The second delivering means can be a deployment tube adapted to push the occlusion device with the distal support structure through the sheath. The material and the configuration of the deployment tube can be the same as described for the first aspect. In an alternative embodiment, the deployment tube can be a wire spring and can comprise at its tip a connecting member which is adapted to be removably connected to the distal support structure of the occlusion device. In this embodiment, the occlusion device can have at its rear end a hollow tube having a threaded exterior surface and the connecting member can have a threaded interior surface to engage at the threaded hollow tube of the distal support structure by a screwing mechanism. This enables the secure connection of the deployment tube with the occlusion device during the deployment procedure. For example, the deployment tube can be used for moving the occlusion device through the catheter to the position of the tissue defect. Alternatively, this deployment tube can be used to deploy the folded distal support structure and to arrange it to the back side of the tissue defect, e.g. the right atrium side. A further alternative use of this second delivering means is the repositioning or retrieval of the occlusion device, if a repositioning procedure or retrieval procedure is necessary. In this regard, the second delivering means can be used to pull back the distal support structure or the total occlusion device into the sheath or the catheter. Thereafter, the occlusion device can again be deployed at the corrected position in the tissue defect or can be retrieved to be replaced by a new one.

The second delivery means can further comprise a polymeric tube, for example, a wire spring, which can be made of a polymeric material. A wire spring is generally flexible enough to be easily inserted in a catheter, but is rigid enough to push the occlusion device into the respective position.

According to a third aspect, a method of closing an anatomical defect in a tissue including, but being not limited to, an opening connecting a front side and a back side of a tissue is provided. In this context, the term "closing an anatomical defect" can mean a surgical treatment of a patient in need of such a treatment or can be an in vitro method where defects at tissues outside the patient can be treated. The method of the third aspect of the invention comprises the steps of providing a sheath into which an occlusion device according to the first aspect has been inserted, moving the occlusion device through the sheath to the site of the anatomical defect by using a delivering means, moving the proximal support structure of the occlusion device out of the sheath through the defect to the front side of the tissue (e.g., left atrium, LA), deploying the proximal support structure at the front side of the tissue to close the defect from the front side, withdrawing the sheath to release the waist portion in the opening and to release the distal support structure at the back side of the tissue, and deploying the distal support structure of the occlusion device at the anatomical defect to close the defect from the back side of the tissue (e.g., right atrium, RA). In the context of the present application, the term "moving" means either pulling the device at their proximal structure or pushing the device at their distal support portion during the insertion of the occlusion device into the sheath or in the proximity of the tissue of the subject to be treated.

In the step of moving the occlusion device out of the sheath and through the front side of the tissue, it is either meant that the sheath goes through the opening while the proximal support structure is moved out of the sheath or the sheath is at the front side of the defect while the proximal support structure is moved out of the sheath.

In an embodiment of the method of this aspect, the proximal and the distal support structure can support a proximal or distal occlusion film, respectively. In this case, the proximal occlusion film is moved together with the proximal support structure and the distal occlusion film is moved together with the distal support structure.

In another embodiment of the method of this aspect, the method can optionally comprise steps of retrieving the occlusion device out of the sheath of the catheter after the proximal support structure has been released from the sheath, for example if the proximal support structure has been released before moving it through the defect or the distal support structure has been released at the front side of the defect. The step of retrieving the delivering system can comprise the steps of retrieving the occlusion device out of the sheath of the catheter and using a new occlusion device in the next step. That means, in one embodiment that if the retrieval of the occlusion device is necessary, a new occlusion device needs to be used and the deployment procedure needs to be repeated again.

In a further embodiment of the third aspect, the step of retrieving the occlusion device can comprise the steps of withdrawing the retrieval wire while holding the sheath in position to force either the proximal support structure and/or the distal support structure of the occlusion device back into the sheath. Alternatively, the retrieving step can be carried out by withdrawing the second delivering means connected to the distal support structure to force either the total occlusion device or the distal support structure of the occlusion device back into the sheath.

It is also within the above definition of the method to use the occlusion device of the first aspect in a transcatheteral closure of an anatomical defect in tissue like a septal defect or shunt in the heart or the vascular system. Septal defect can be in this context any defect including, but being not limited to, atrial septal defects, ventricular septal defects, patent ductus arteriosus, or patent foramen ovale.

Figure 2:
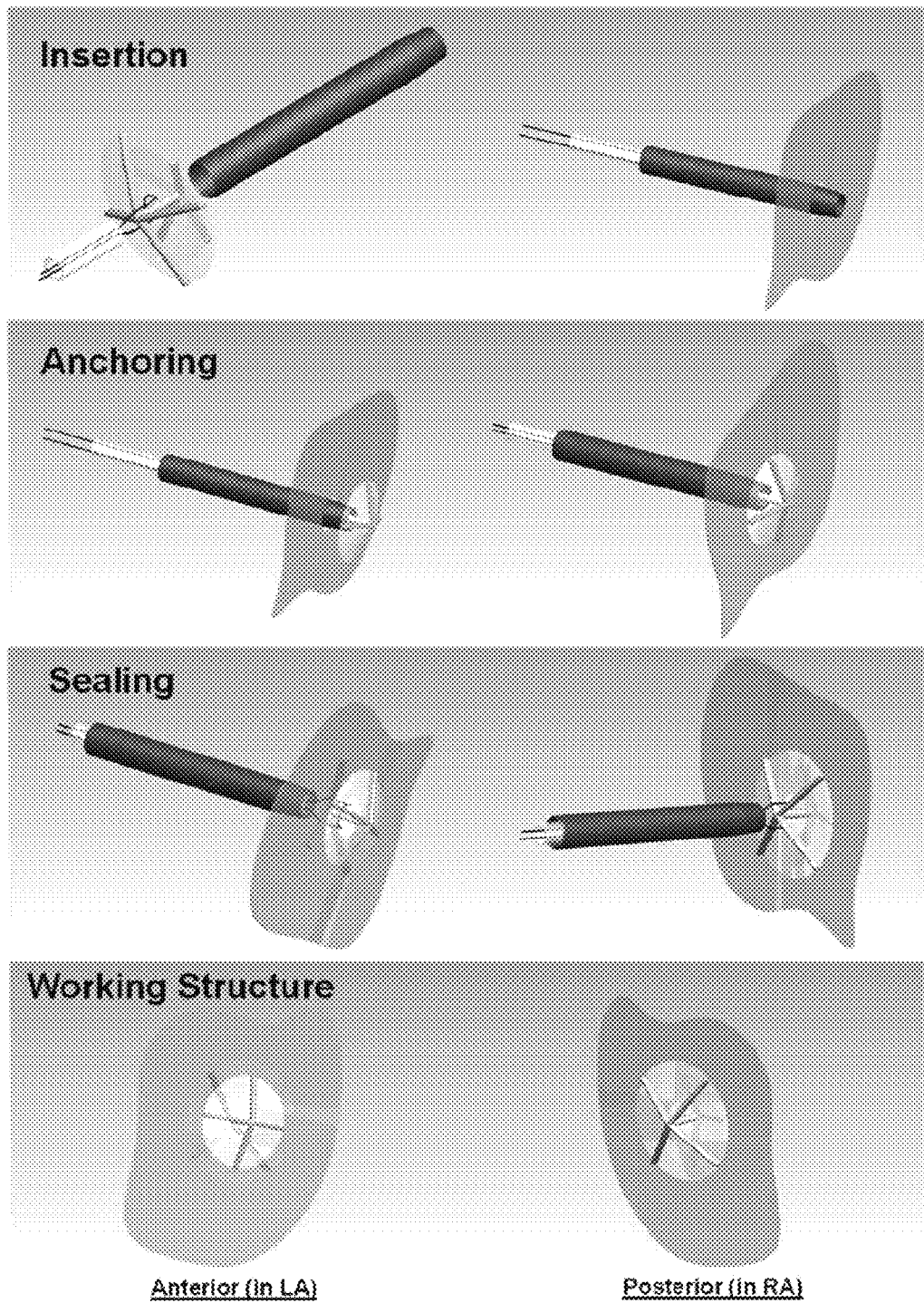
FIG. 2 shows the main steps of the deployment procedure for an embodiment of the occlusion device described herein.
Figure 3:
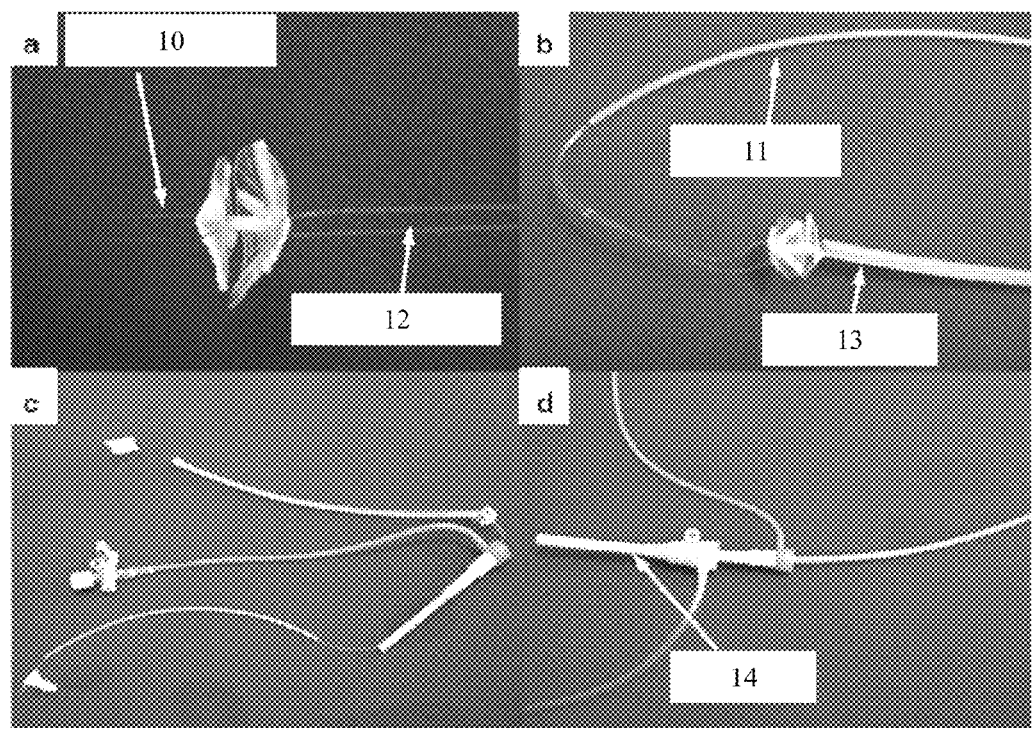
FIGS. 3 a-d show the preparation steps of the occlusion device described herein. In these Figures, the occlusion device of an embodiment described herein is provided with parts of a delivering system.

The deployment procedure of an occlusion device of the first aspect which is covered by the third aspect of the present invention comprises in a particular embodiment which is shown in FIG. 2 the steps of insertion, anchoring, optionally repositioning, sealing, optionally retrieving of the occlusion device of the first aspect (as shown in FIG. 3) by means of the delivering system described beforehand, and then retrieving the delivering system. In the FIG. 2, the procedure is described on the basis of an in vitro method, wherein an opening in a tissue (grey) is closed. The method generally comprises the following steps:

1) Device Preparation

The occlusion device can be assembled with the delivering system, i.e. with the loading wire (10), the guide tube (11), the retrieval wire (12), and the deployment tube (13) as described above or can still be provided in a preloaded state, for example in the form of being already loaded in a sheath (14) of a catheter. At first the loading wire (10) can be removably connected to the proximal support structure of the occlusion device. This can for example be done by anchoring the wire by using the joint of the spokes and the waist portion as anchor points. At next, the loading wire (10) can be inserted into a guide tube (11) for guiding the loading wire (10) through the sheath (14) during the insertion step. In the embodiment shown in FIG. 2, the loading wire (10) and the guide tube (11) are not shown. However, this can be derived from the FIG. 3b where at the left side of the occlusion device the loading wire (10) and the guide tube (11) connected to the proximal support structure are shown. In FIG. 3c, the guide tube (11) has been completely moved through the sheath (14), while the loading wire (10) has been inserted into the sheath (14). Then the guide tube (11) can be removed at this step or after the insertion step.

In a next preparation step, the retrieval wire (12) can be removably connected to the distal support structure and housed in the deployment tube as it is shown in the first picture of FIG. 2 as well as in FIG. 3b, right-hand side.

2) Insertion

The loading wire (10) is used to pull the occlusion device in a folded state into and to the end of the sheath (14) of a catheter beginning with the proximal support structure, followed by the waist portion and the distal support structure. The catheter sheath (14) used in this embodiment can be, for example, a sheath usually used for heart catheter applications like an 11F sheath.

After the entire occlusion device has been inserted into the sheath (14), the loading wire (10) can be removed by pulling at one end of the loop-formed loading wire. If not yet removed, the guide tube (11) can simultaneously be removed from the occlusion device at this step. The prepared occlusion device inserted into the sheath (14) which can be put into another catheter sheath or directly used as catheter sheath is shown in FIG. 3d.

The occlusion device can thereafter be guided by pushing it with the deployment tube (13) to the end of the sheath (14) which can be shortly behind the opening to be closed, that means the sheath (14) advances across the opening so that the proximal support structure and the proximal occlusion film are prepared to can be pushed through the defect to the front side.

3) Anchoring

The occlusion device can be pushed through the defect to the front side of the opening by means of the deployment tube (13). After the proximal support structure has been released from the sheath (14), the support structure springs open, for example, springs in its originally unfolded shape due to the shape memory property of the material of the support structure, and, thereby, unfolds the proximal occlusion film. Thereafter the sheath (14) and the retrieval wire (12) are held together and both of them are pulled back until the unfolded proximal support structure and the proximal occlusion film have been anchored at the front side, thereby sealing the defect from the front side of the septum. The correct position can be checked by a respective "anchoring pull" at both of the sheath (14) and the retrieval wire (12). If the proximal support structure has been anchored at the front side, the anchoring pull feedback is felt when the proximal support structure sits against the tissue at the front side of the tissue.

The position of the deployed proximal support structure is shown in FIG. 2 in the section "Anchoring".

4) Reposition

If the proximal support structure is for example released wrongly, for example is not pushed through the opening, but has been opened before the defect, or if the position of the occlusion device should be repositioned due to another reason, the sheath (14) can be held in position while the retrieval wire (12) can be moved back, e.g. by pulling action, to force the occlusion device back into the sheath.

The occlusion device thus treated can then be replaced with a new occlusion device and the re-anchoring step (step 3) of the occlusion device can be performed again.

5) Sealing

If the anchoring is satisfactory, hold the retrieval wire (12) in position and push the deployment tube (13) slightly against the distal support structure and the distal occlusion film which are still folded in the sheath (14). Withdraw the sheath (14) further to release the waist portion, the distal support structure and the distal occlusion film from the sheath. Thereby the waist portion is brought within the opening and the distal support structure is allowed to spring automatically open. This can, for example, be managed by a sufficient rigidity of the material and the respective stress in the folded state or by shape memory properties of the respective support structure material.

The distal support structure automatically opens its folded parts such that the distal occlusion film seals the defect from the back side of the tissue. Alternatively, any other unfolding mechanism can be used as long as the support structure can sufficiently be unfolded as it is shown in the Figure under the item "Sealing".

As shown in FIG. 2, the distal support structure closes the opening from the back side of the defect.

6) Device Retrieval

If the distal support structure has, for example, accidently been released behind the defect in step 5, that means at the front side of the defect, the retrieval wire (12) can be moved back, e.g., by pulling action, while holding the sheath (14) in position. Thereby the occlusion device can be forced back into the sheath (14) by using the rim of the sheath to fold the support structures again. Then, the occlusion device can be replaced with a new occlusion device and the deployment procedure can start again with step 1.

7) Removal of Delivering System

If step 5 has been satisfactory, the retrieval wire (12) can be removed, for example, by pulling at one end of the retrieval wire (12), if it is in looped form. Afterwards the deployment tube (13) and the sheath (14) can also be pulled back to retrieve all parts of the delivering system and to leave the occlusion device in its folded working structure locked by means of the proximal support structure and the distal support structure provided at the front side and the back side of the defect, respectively.

Figure 34A:
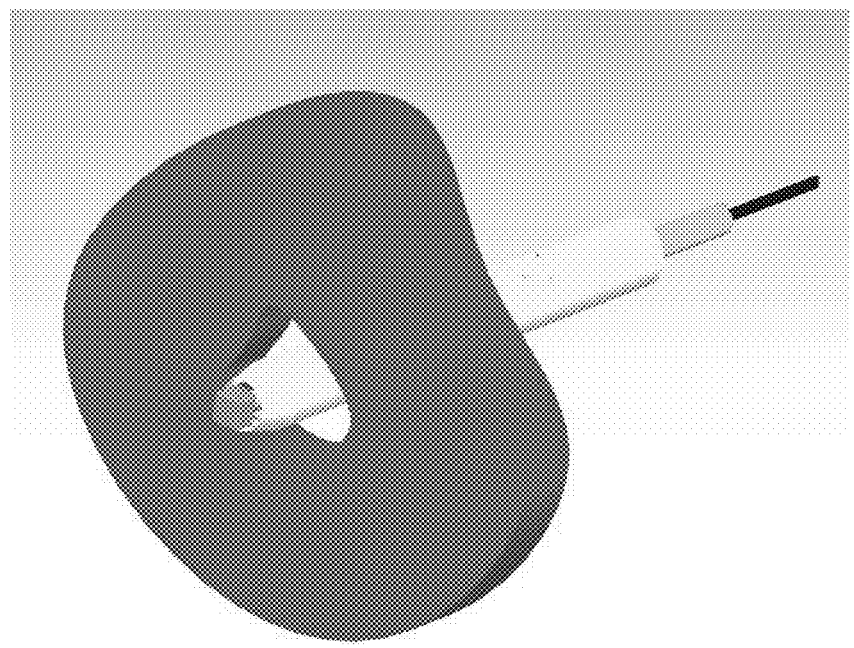
FIGS. 34a-f show the deployment process of an occlusion device of the second aspect at a model of a tissue defect.
Figure 34B:
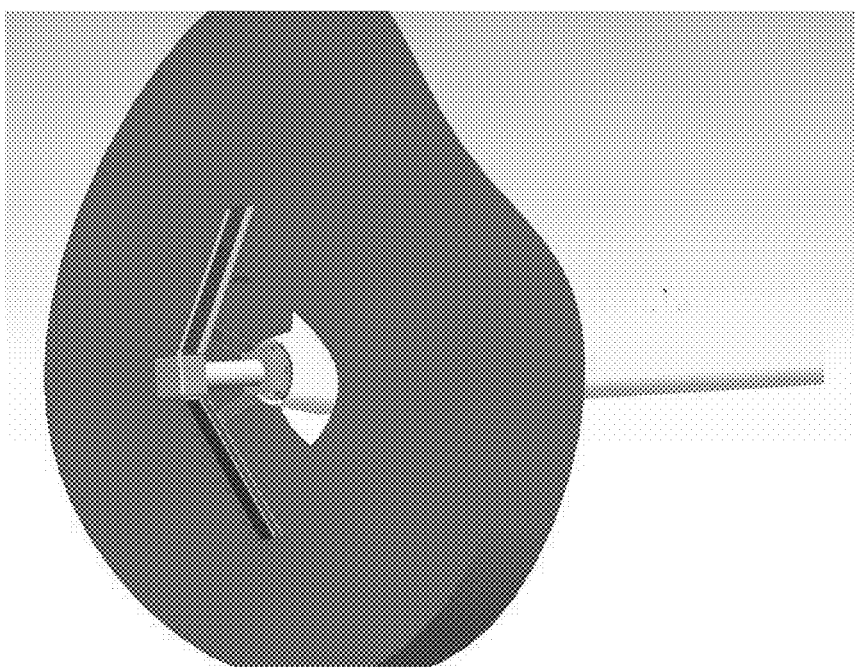
Figure 34C:
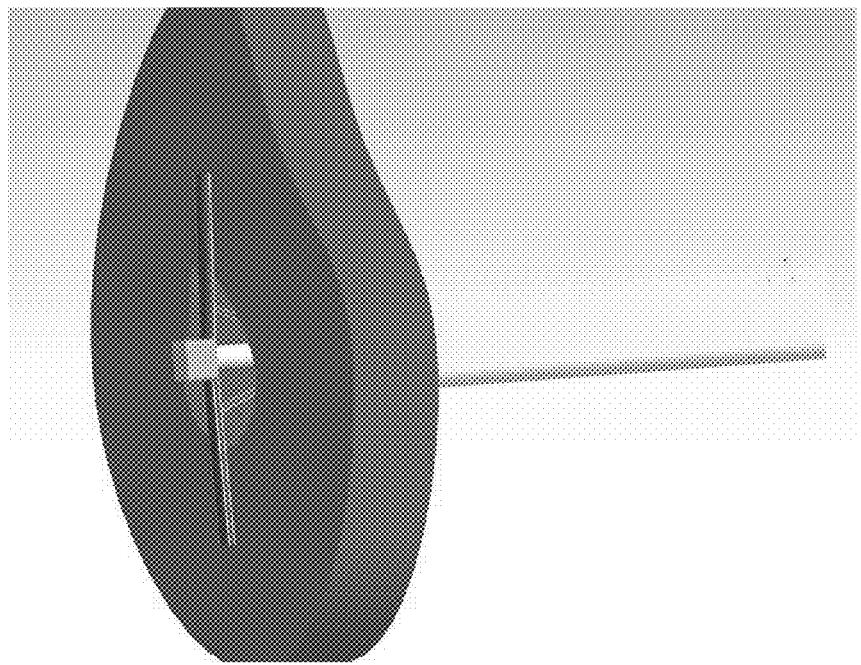
Figure 34D:
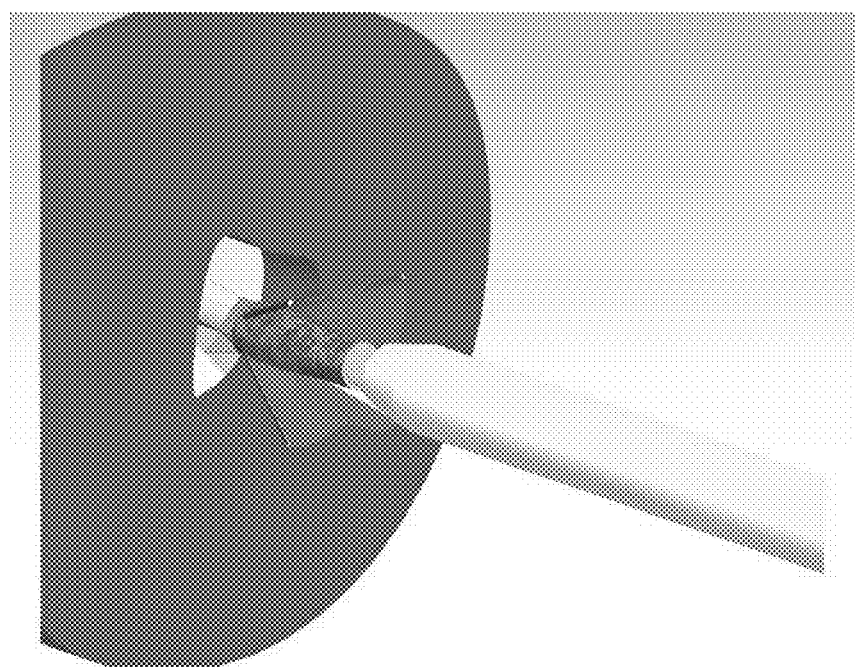
Figure 34E:
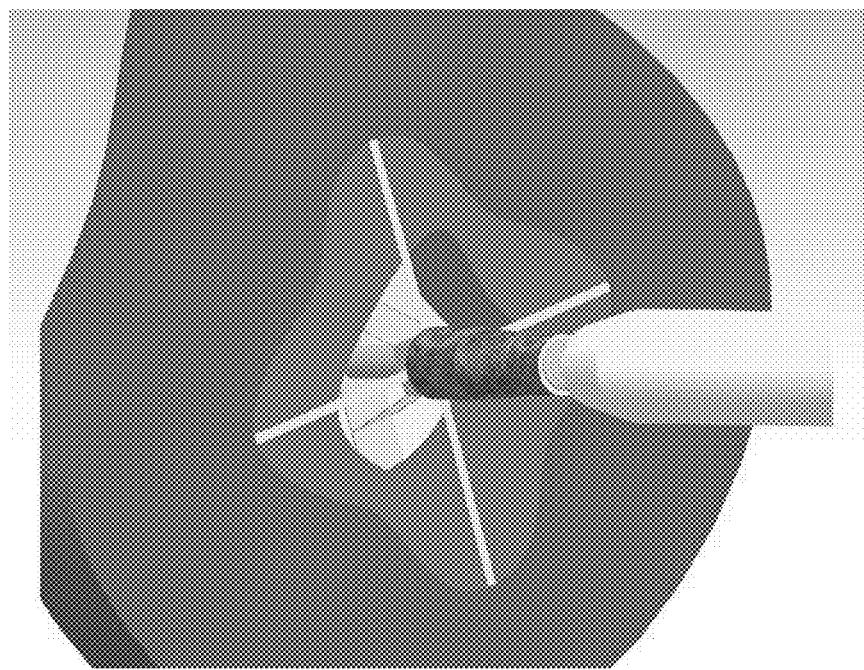
Figure 34F:
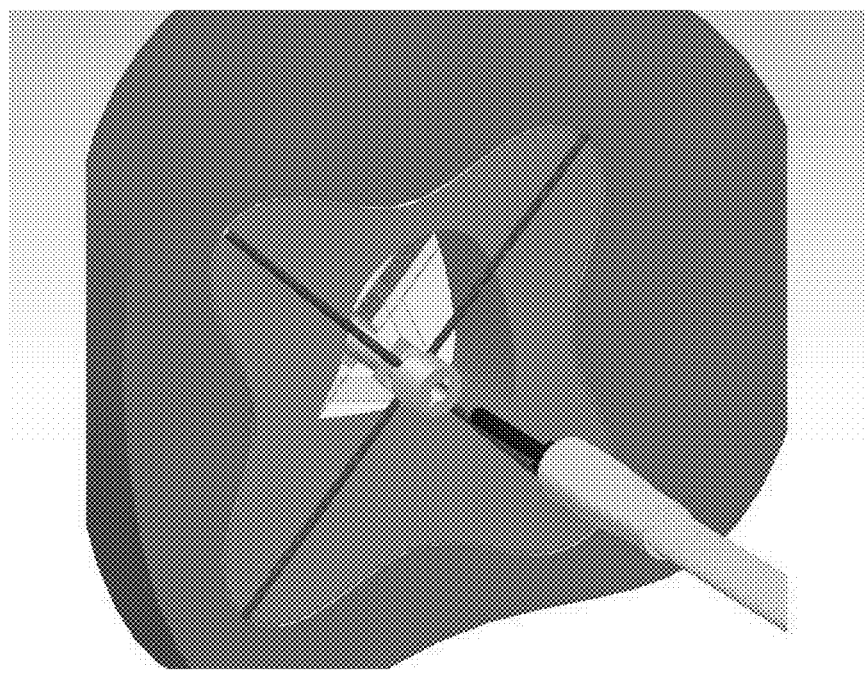

The deployment procedure of an occlusion device of the second aspect which is also covered by the third aspect of the present invention comprises in a particular embodiment shown in FIGS. 34 a-f the following steps: a step of positioning the sheath including the folded occlusion device at the tissue defect (see FIG. 34a), deploying the proximal support structure at the front side of the defect by pulling the sheath back until the proximal support structure is released (see FIG. 34b), anchoring the unfolded proximal support structure at the front side of the defect (see FIG. 34c), deploying the distal support structure at the back side of the defect by pulling the sheath back until the distal support structure is released, while the folded distal support structure will be recovered into its original form due to shape-memory effects (as shown in FIG. 34d), anchoring the unfolded distal support structure at the back side of the defect (as shown in FIG. 34e), and retrieving the delivering system (see FIG. 340. In FIG. 34, the deployment process is described at a model, which could, for example, be used in an in vitro method, wherein an opening in a tissue (grey) is closed.

In the following the present invention is described in detail by the following non-limiting Examples. Of course the present invention is not limited to these embodiments and the skilled person knows several modifications and equivalent embodiments of the occlusion device when considering the above detailed description of the invention.

Example 1

Figure 4:
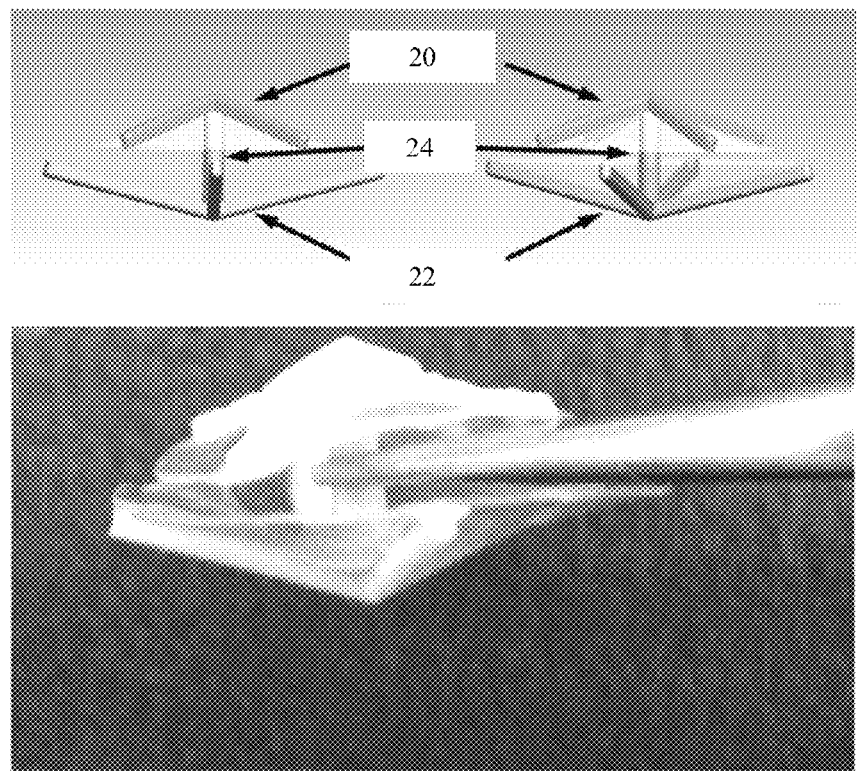
FIG. 4 shows an embodiment of an occlusion device described herein.

In FIG. 4, an embodiment of an occlusion device of the first aspect is shown which has been adjusted for the use as an ASD/PFO occluder. The occlusion device of this embodiment comprises a proximal support structure together with a proximal occlusion film in disc-like form (20). Both structural parts are integrally formed, wherein the spokes of the proximal support structure are white due to their higher amount of radiopacifier. The occlusion device of this embodiment further comprises a waist portion (24) connected to the proximal support structure. At the other site of the waist portion (24), the distal support structure together with a distal occlusion film in disc-like form (22) is connected to the waist portion (24). The proximal structural parts including the optional proximal occlusion film, the waist portion, and the distal structural parts including the distal occlusion film have been adapted to be positioned into the left atrium (LA), ASD/PFO tunnel (the "opening" or "defect") and right atrium (RA), respectively. The disc-like proximal and distal ends of the occlusion device are shown in FIG. 4 in their unfolded state, which means they are in their working structure as when they would seal the ASD/PFO. However, the disc-like proximal and distal structures are adjusted such that they can be folded into a sheath and can be delivered to the defect via transcatheter procedure as described beforehand.

In this embodiment, the occlusion device has also been provided with a good visibility in fluoroscopy. For providing at least partly radiopacity, the proximal and the distal support structure of the occlusion device have been provided with $BaSO_4$ as radiopacifier. Thereby, radiopacity has been provided to the occlusion device.

Alternatively, also the other portions of the films could be made of a material comprising a radiopacifier to make the device visible during the deployment procedure.

Example 2

Fabrication Process

Figure 5:
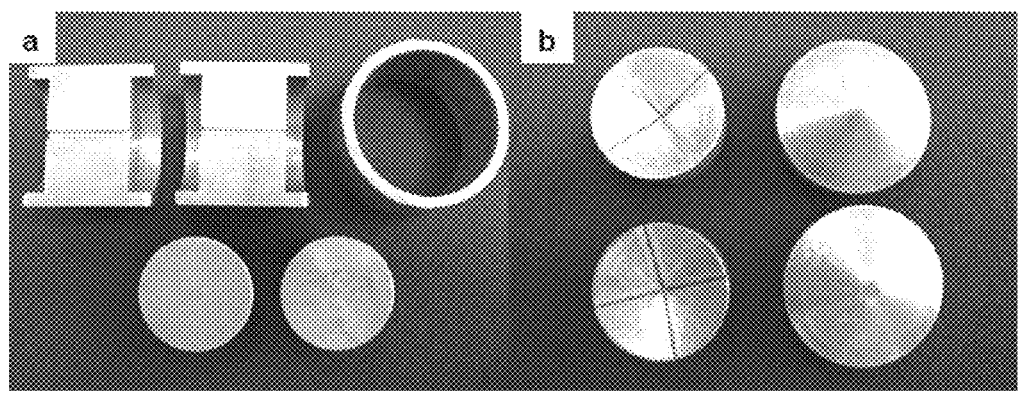

Pure PLA-PCL copolymer displays the highest degree of flexibility. Hence it has been selected as the major material to construct the occlusion device in this embodiment. Different ratios of $BaSO_4$ can generally be added to achieve X-ray visibility (radiopacity). A hot pressing technique has been developed to fabricate the occlusion device. The mould sets used in the process are shown in FIG. 5. In this Figure, the mould for hot pressing is adapted such that the proximal and the distal support structure consist of four spokes, respectively. The mould sets for the waist portion and the respective LA and RA disc structures are shown in FIG. 5a and FIG. 5b, respectively. In FIG. 5b, each mould has a respective disc-shape and comprises four linear grooves outwardly extending from the middle of one of the moulds of each set for the spokes.

1) Fabrication of Waist Portion (24)

Figure 6:
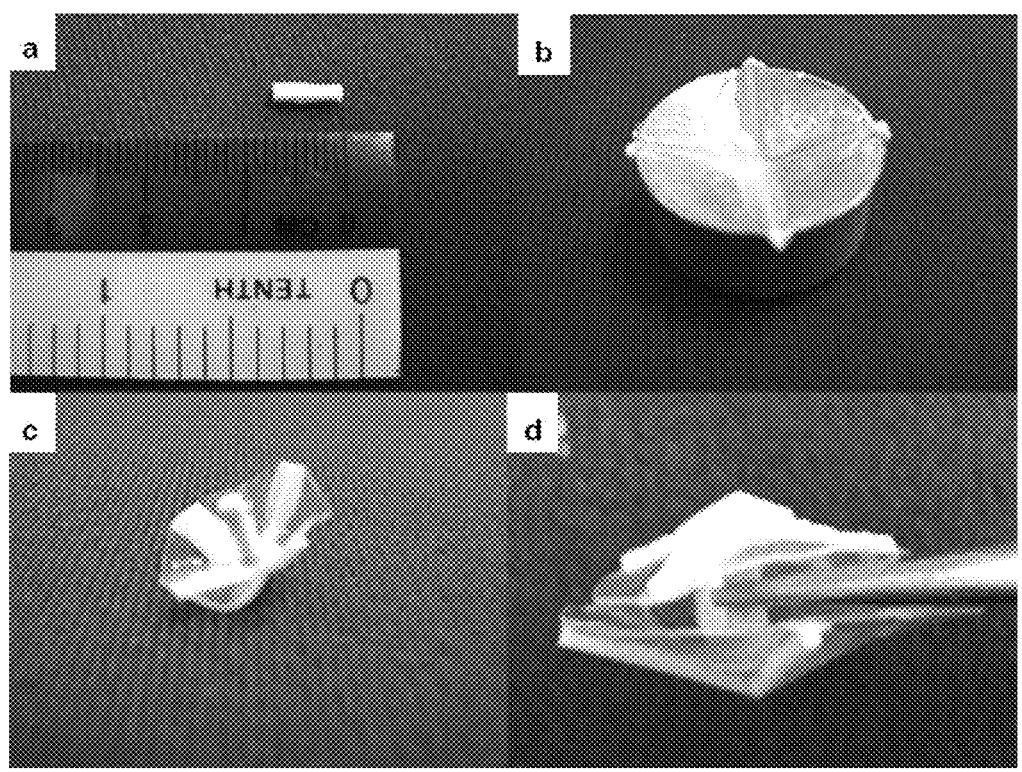
FIGS. 6 a-d show the respective manufacturing steps of an occlusion device described herein.

The waist portion (24) in the form of a stem was molded using PLA-PCL copolymer with 30% $BaSO_4$. The final dimension of the waist portion was a diameter of 1.2 mm and a length of 7 mm as shown in FIG. 6a.

2) Fabrication of LA Disc (20)

The LA disc (shown in FIG. 6b) comprises the proximal support structure and the proximal occlusion film. The LA disc was molded in a four-spoke construct. PCL (with 30% $BaSO_4$) was used for spokes (cross-section of 0.6 mm wide× 0.8 mm high) for enhanced anchoring capability and pure copolymer film (cross-section of 14 mm, 200 μm thick) was used for the film section of the occlusion device. This material has suitable flexibility so that it can be folded well.

3) Fabrication of RA Disc (22)

The RA disc was constructed in a similar manner as the LA disc. PLA-PCL copolymer (with 30% $BaSO_4$) was used for spokes (cross-section of 0.6 mm wide×0.8 mm high) and pure copolymer film (cross section of 16 mm, 200 μm thick) was used for the film section of the distal occlusion film.

4) Connection of the Waist Portion and Both Discs

Finally the waist portion in the form of a stem and both discs were thermally fused and connected and a complete occlusion device as described herein was obtained as shown in FIG. 6c (LA disc attached to the stem) and FIG. 6d (complete occlusion device).

The thus prepared occlusion device can be loaded into a sheath as described beforehand by using the respective delivering system.

Example 3

Sterilization Procedure

Ethylene oxide (ETO) sterilization of the devices and associated surgical tools was done at Tan Tock Seng Hospital, Singapore. Devices and relevant delivering systems were sealed in the form of the kit of the present invention comprising the occlusion device including the delivering system in a standard ETO sterilization pouch. The sterilization procedure was conducted at 37° C. for six hours followed by purging of the ETO gas for another continuous 16 hours.

Post-sterilization cell culture conducted both in house and at a contract research lab shows that the procedure complies with relevant standards.

Example 4

In Vitro Testing and Degradation

In Vitro Degradation

Polycaprolactone (PCL Mw 80,000, Aldrich) and PLA-PCL copolymer (IV 1.62, Purac) were studied in vitro for their degradation behavior. Four configurations of films were tested: Pure PCL (200 μm thick); pure copolymer (200 μm thick); PCL with 30% $BaSO_4$ (200 μm thick) and copolymer with 30% $BaSO_4$ (200 μm thick). Films were prepared by solution casting and all films were tested on a thermogravimetric analyser (TGA) to ensure that the solvent content was less than 1% (w/w) before the in vitro tests. Then, 1×1 cm casted films are immersed in phosphate buffer solution (PBS) and stored in an incubator at 37° C. for 12 weeks. Sampling was conducted in duplicate at different time intervals: week 0, week 1, week 4, week 8, and week 12.

Scanning Electron Microscope (SEM) Examination

Figure 7:
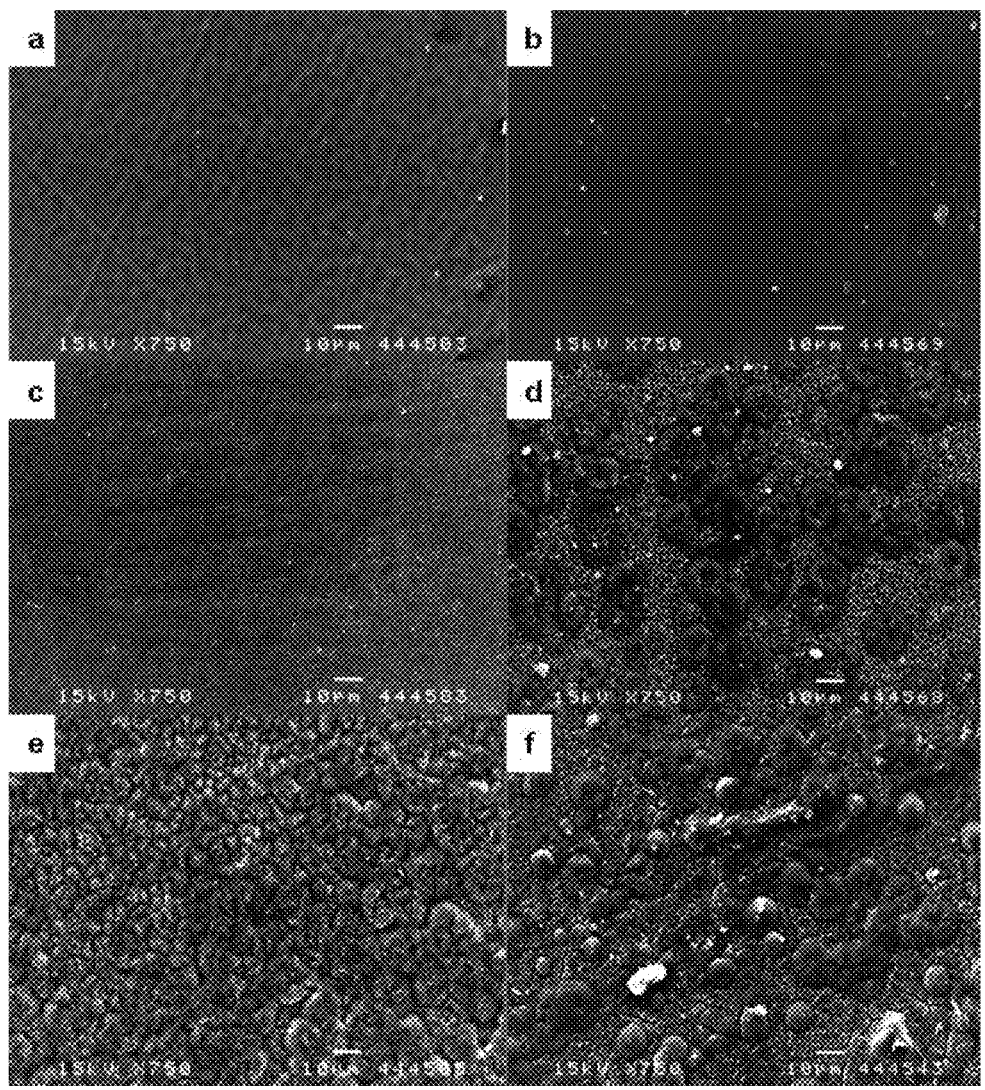
FIGS. 7 a-f show the degradation of pure copolymer: (a) original; (b) 0 week; (c) 1 week; (d) 4 weeks; (e) 8 weeks; (f) 12 weeks (the scale bar is 10 μm).

FIGS. 7a-f show the degradation of pure copolymer. The original copolymer is shown in FIG. 7a. Even after 1 day of immersion, the film surface became smooth (FIG. 7b). After one week, the film was rough again (FIG. 7c). From then on, there occurred many large hilly lumps on the film surface (FIG. 7d) and the lumps were reduced and increased with degradation (FIG. 7e). After 12 weeks, the large lumps occurred again and between them many cracks can be seen (FIG. 7f).

Figure 8:
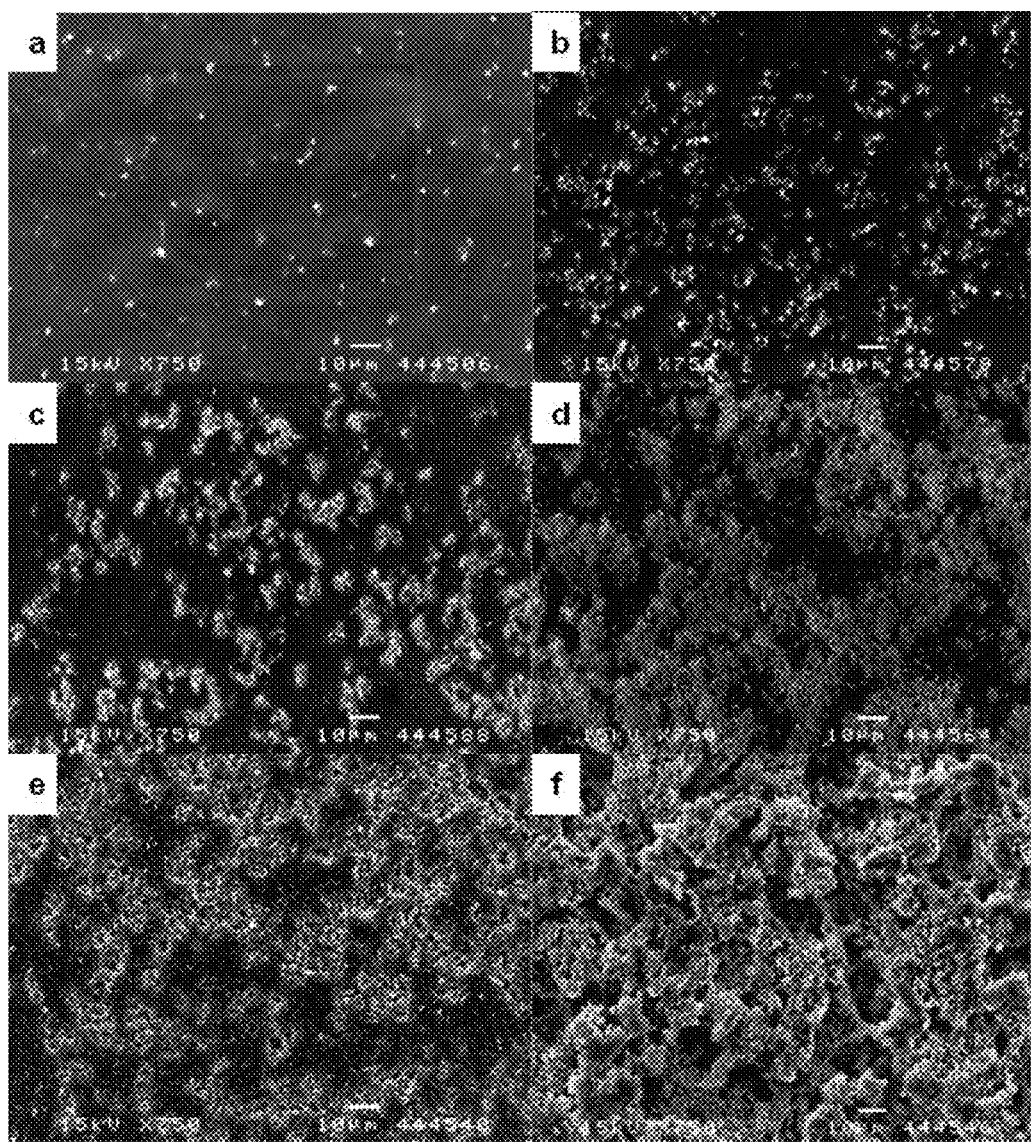
FIGS. 8 a-f show the degradation of copolymer +30% $BaSO_4$: (a) original; (b) 0 week; (c) 1 week; (d) 4 weeks; (e) 8 weeks; (f) 12 weeks (the scale bar is 10 μm).

FIGS. 8a-f show the degradation of copolymer +30% $BaSO_4$. The $BaSO_4$ particles can be clearly seen on the surface of the original film (FIG. 8a). During one week of degradation, the $BaSO_4$ particles were more and more segregated on the surface (FIGS. 8b & c) when the copolymer degraded. Then the particles began to leave the polymer surface, leaving many holes on the film surface (FIG. 8d). Newer $BaSO_4$ particles then appeared on the surface when the degradation continued (FIG. 8e). After 12 weeks, the surface was filled with deep holes (FIG. 8f).

Figure 9:
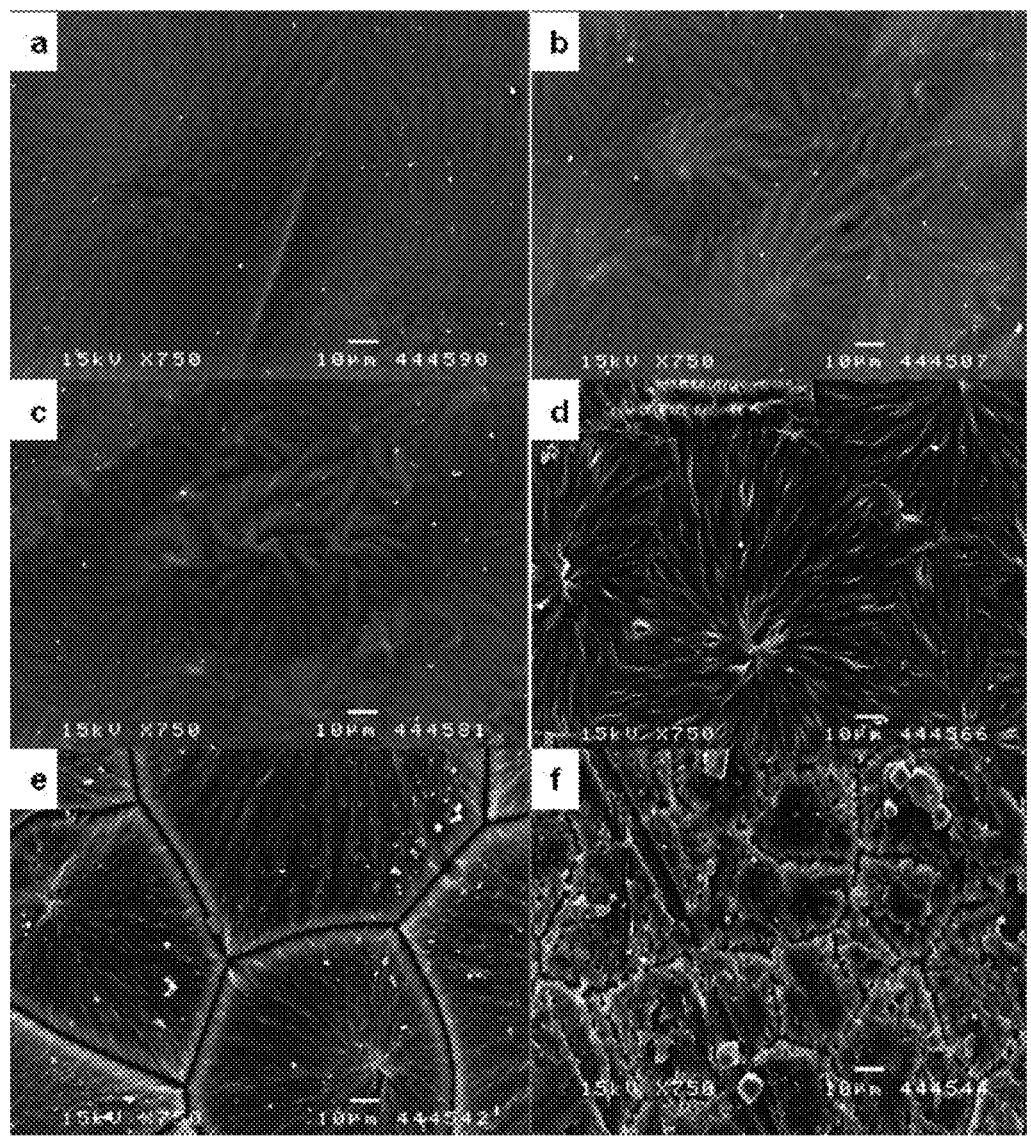
FIGS. 9 a-f show the degradation of PCL: (a) original; (b) 0 week; (c) 1 week; (d) 4 weeks; (e) 8 weeks; (f) 12 weeks (the scale bar is 10 μm).

FIGS. 9a-f show the degradation of pure PCL. The film surface remained almost intact for one week. Figures a-c show the surface in the original state, after 0 week and after 1 week. After 4 weeks the surface was composed of large chrysanthemum-like "cells" with clear margins between them (FIG. 9d). The margins became deep and widen with degradation and the cells were separated from each other like the classic crystal structure (FIG. 9e). At 12 weeks, the large cells disappeared and were divided into many smaller cells (FIG. 9f).

Figure 10:
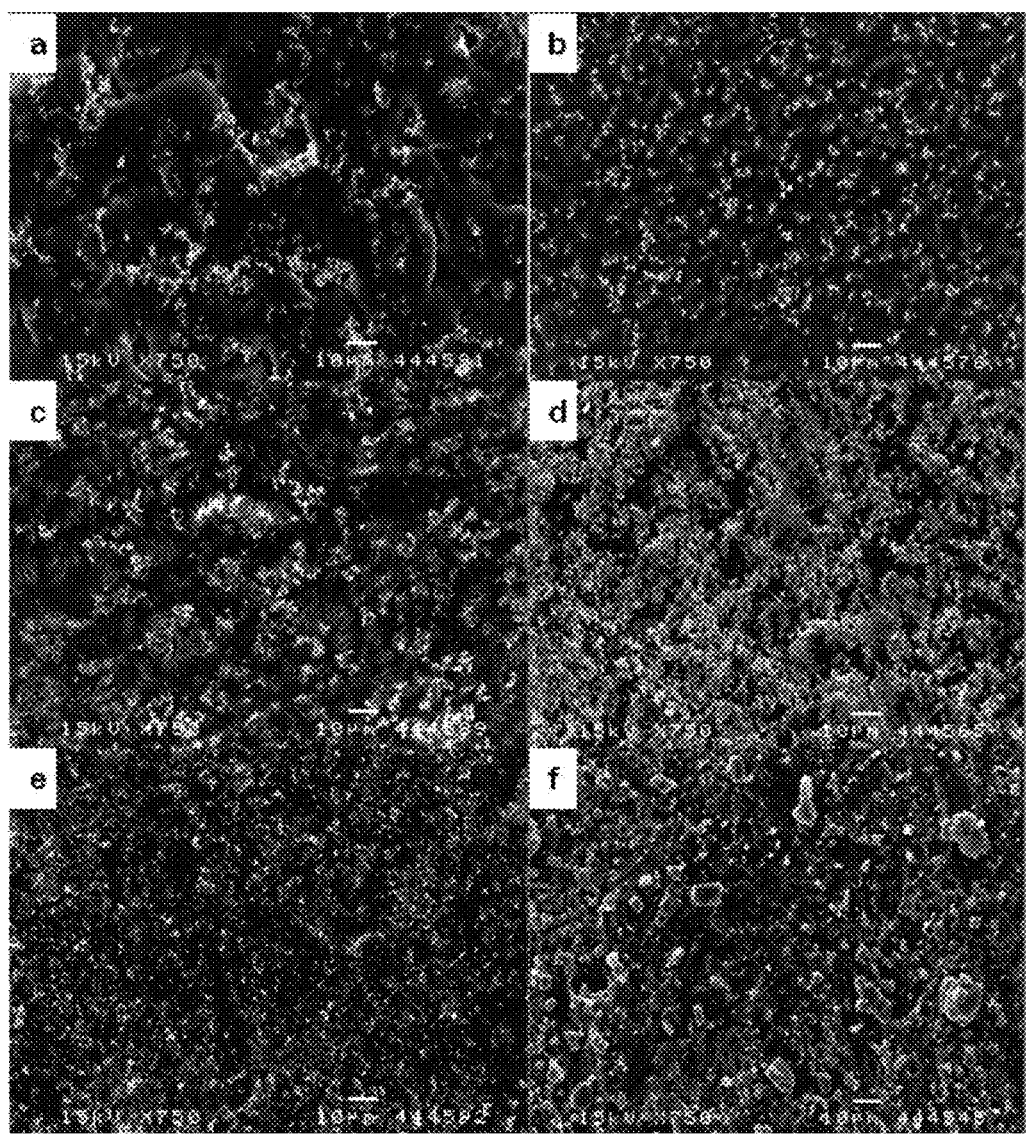
FIGS. 10 a-f show the degradation of PCL+30% $BaSO_4$: (a) original; (b) 0 week; (c) 1 week; (d) 4 weeks; (e) 8 weeks; (f) 12 weeks (the scale bar is 10 μm).

FIGS. 10a-f show the degradation of PCL+30% $BaSO_4$. It can be seen that the $BaSO_4$ particles were more dispersed than in the copolymer matrix in the original state (FIG. 10a). The degradation process was similar to that of the copolymer +30% $BaSO_4$. The $BaSO_4$ particles became more and more segregated until they eluted out of the film, leaving many tiny pores on the surface. FIGS. 10b-d show the respective surface state after 0, 1 and 4 weeks. Then new $BaSO_4$ particles surfaced with degradation (FIG. 10e). After 12 weeks the film surface were filled with tiny holes but were not as deep as that on the copolymer matrix (FIG. 10f).

Molecular Weight Loss

The molecular weight (Mw) of each sample collected from time points was tested on gel permeation chromatography (GPC).

Figure 11:
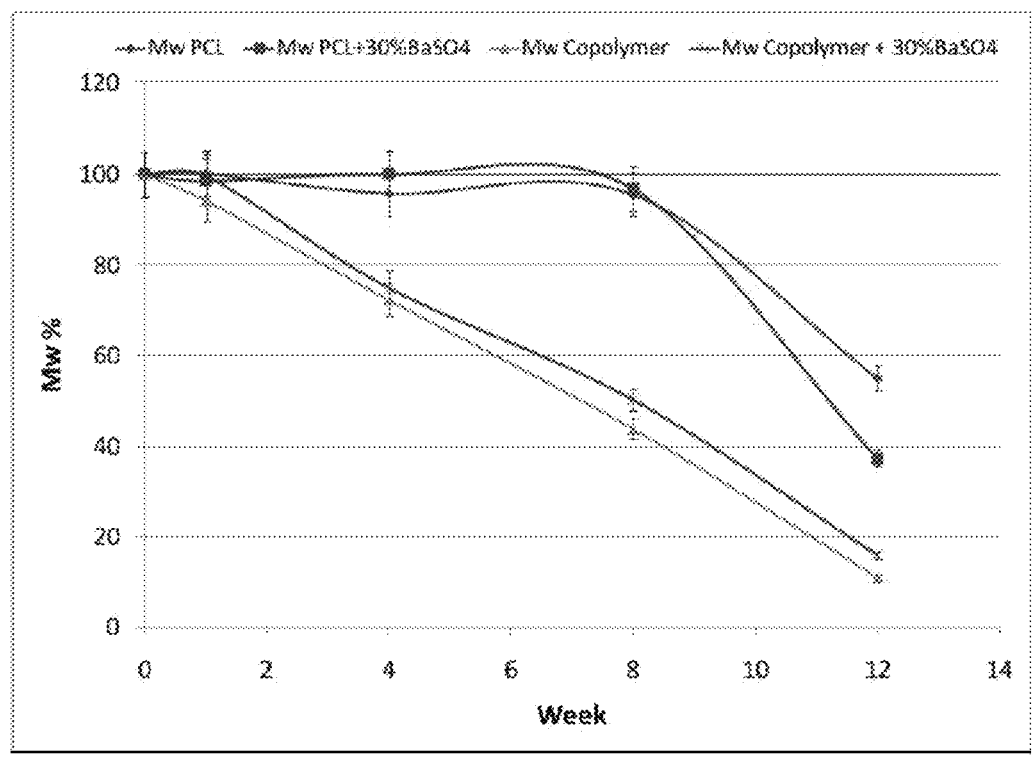
FIG. 11 shows the molecular weight (Mw) loss during 12 weeks of degradation of some polymer candidates which can be used in occlusion devices described herein.

Mw loss of four types of films was plotted in FIG. 11. Copolymer degrades generally faster than PCL as expected up to week 12. PCL starts to show rapid degradation after week 8, while copolymer displays steady chain shortening pattern from week 1 onwards. PCL starts to accelerate on degradation rate after week 8, while copolymer shows a linear Mw loss throughout 12 weeks. And $BaSO_4$, as the physical inclusion, does not seem to impact significantly on the degradation pattern of the polymers.

Mass Loss

The mass loss of films after each time point was measured after the samples were recovered from the PBS and freeze dried.

Figure 12:
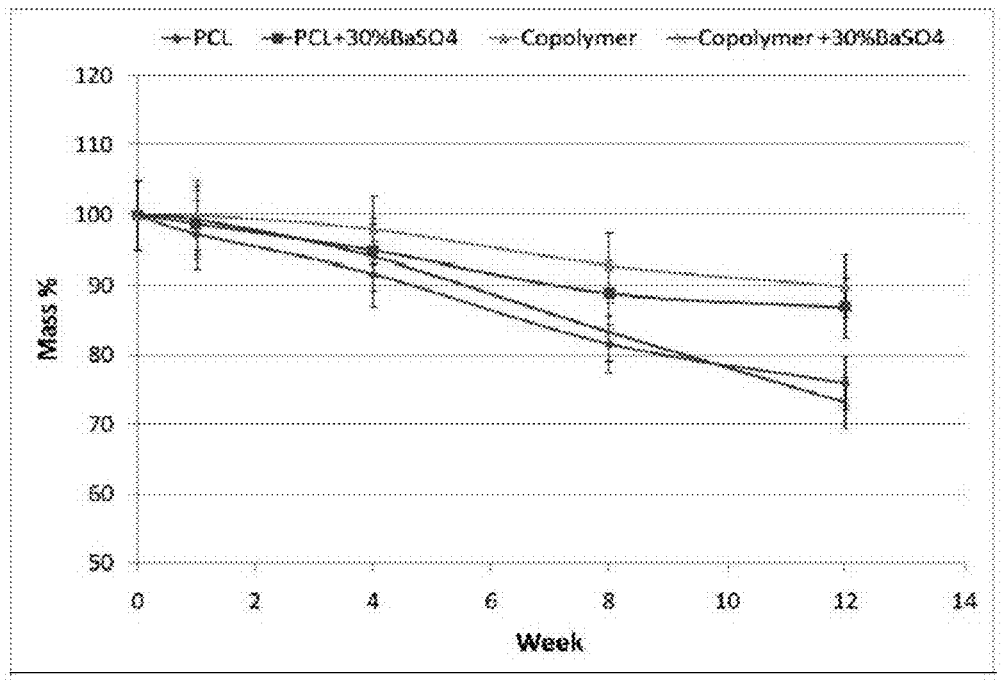
FIG. 12 shows the mass loss (in percentage of the original probe) during 12 weeks of degradation of the polymer candidates used for the measurements of FIG. 11.

An increase in mass loss for the PCL films was observed as degradation continues. (FIG. 12). And copolymer films show a more steady and linear trend.

Modulus Change

DMA test for storage modulus change was also conducted at each time point at 37° C. All samples were immersed in deionized water for 20 min prior to loading on DMA. DMA runs were performed at Multi Frequency Strain mode from 25° C. to 100° C. for copolymer based films And 25° C. to 60° C. for PCL based films.

Figure 13:
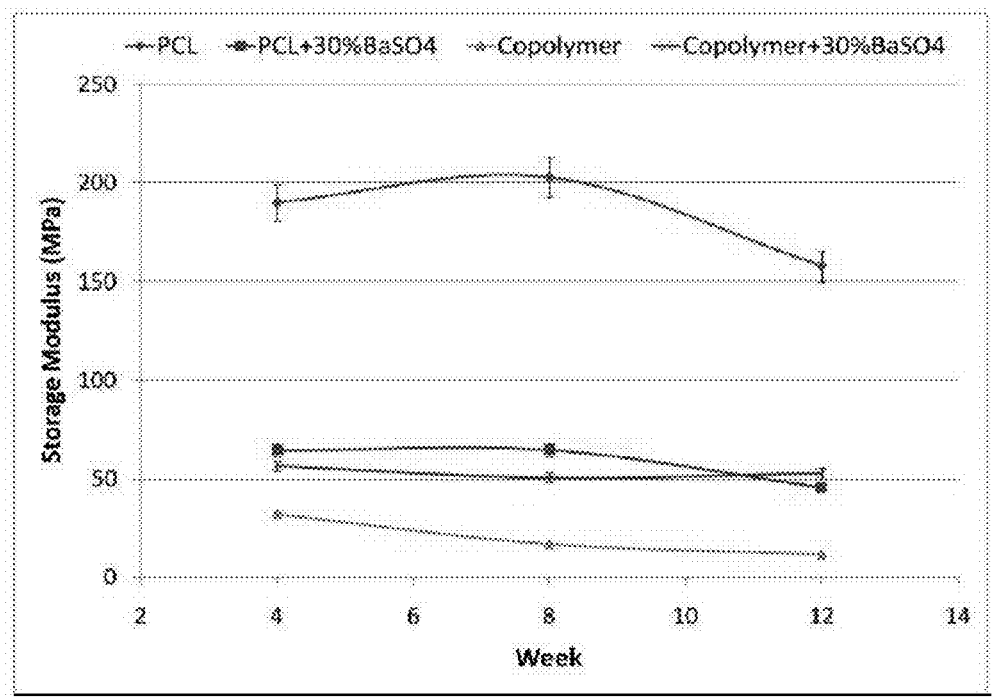
FIG. 13 shows the storage modulus variation (in MPa) at 37° C. during 12 weeks of degradation of the polymer candidates used for the measurements of FIG. 11.

The mechanical property is closely linked with the molecular weight of a (co)polymer. As degradation progresses, molecular weight loss should result in modulus loss of the polymers. However, modulus change surprisingly did not match the degree of molecular weight loss. This is shown in FIG. 13. Most likely, the molecular weight loss occurs in the amorphous region, and is not substantial enough to decrease modulus, which may be dominated by crystallinity for PCL; for the copolymer, some loss in modulus can be seen in FIG. 13. However, it did match with the in vivo results as after one-month implantation (swines have higher metabolism so comparable to three months in humans) the polymers retain good integrity and enough load bearing quality for its function.

Example 5

Figure 14:
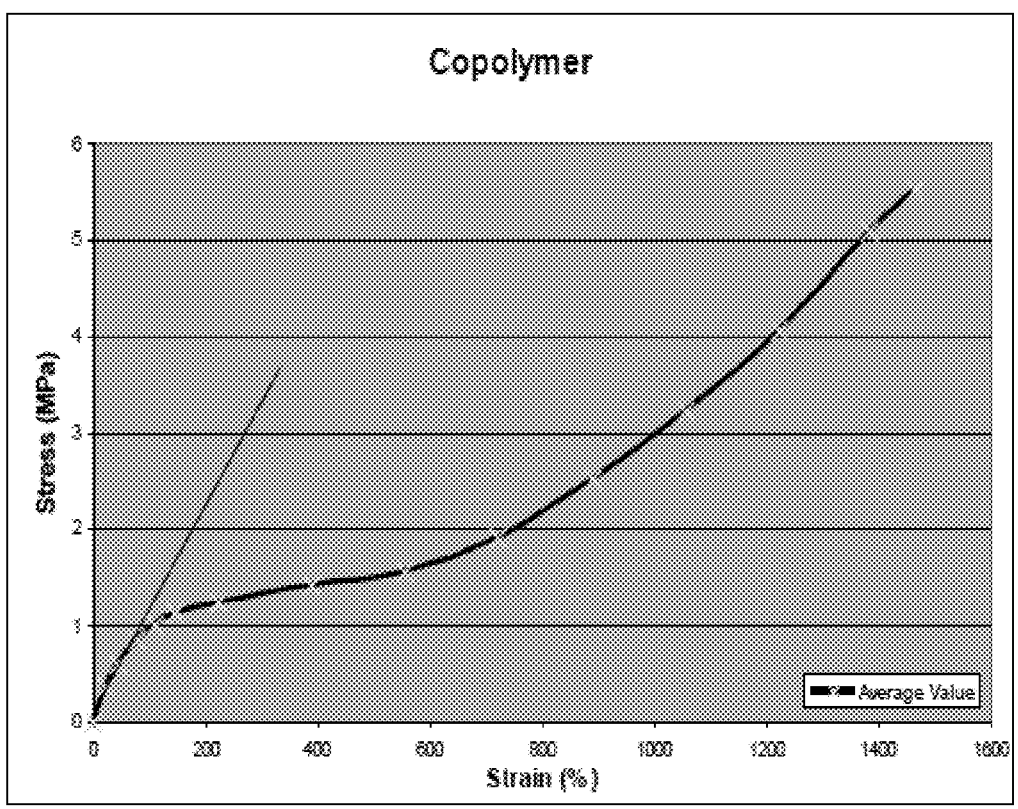
FIG. 14 shows the stress-strain curve of a copolymer of polylactic acid and polycaprolactone (PLA-PCL copolymer) 70/30.

As pure PLA was considered to be too stiff for this application, it was blended into the PLA-PCL copolymer at certain ratios and the Young's moduli were determined by Instron. The test was done with a load cell of 100 N at a loading rate of 55 min/min (fastest equipment limit). The films were cut in 41×5 mm size and gripped with an effective gauge length of 5 mm (to ensure maximum stretching distance). Stress-strain curve was plotted accordingly where the Young's modulus could be obtained for each sample (FIG. 14).

Young's moduli of different material combinations were calculated and listed as shown in Table 2.

TABLE 2

Young's Moduli of polymers and their blends

| No. | Materials | Young's Modulus (MPa) |
|---|---|---|
| 1 | Pure copolymer | 0.92 |
| 2 | Pure PCL | 166.10 |
| 3 | Copolymer with 30% $BaSO_4$ | 10.55 |
| 4 | Copolymer blend with PLA (80% copolymer/ 20% PLA) | 5 |
| 5 | Copolymer blend with PLA (60/40) | 66.54 |
| 6 | Copolymer blend with PLGA (80% copolymer/ 20% PLGA) | 4.21 |
| 7 | Copolymer blend with PLGA (60/40) | 53.47 |

All the films did not break at the maximum elongation limit of the equipment (results not shown). For example, the copolymer film did not reach the breaking point even at the maximum strain rate (55 mm/min) when total strain was more than 1200%, displaying an extraordinary flexibility, which is highly desired for the occluder design of the first aspect. PLA-PCL copolymer blend with PLA resulted in highest Young's modulus among all. The increment of modulus also increased tremendously with the increasing amount of PLA. Similar trend is observed among $BaSO_4$ and PLGA blended copolymer. And the excellent stretchability of more than 1200% elongation was still observed among all other blends.

Figure 15A:
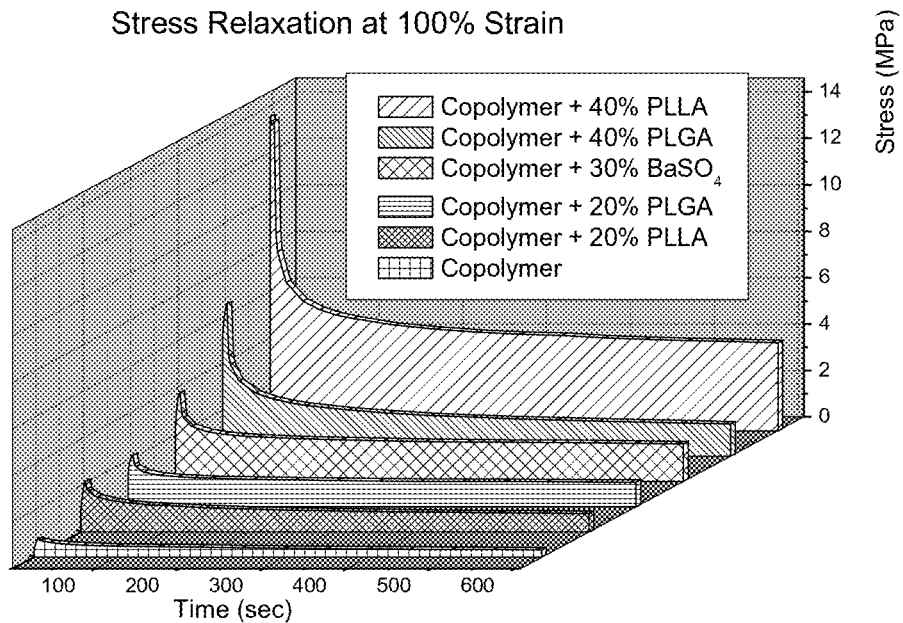
FIG. 15a shows the stress relaxation curve of 100% strain and FIG. 15b shows the stress-relaxation curve of 200% strain.
Figure 15B:
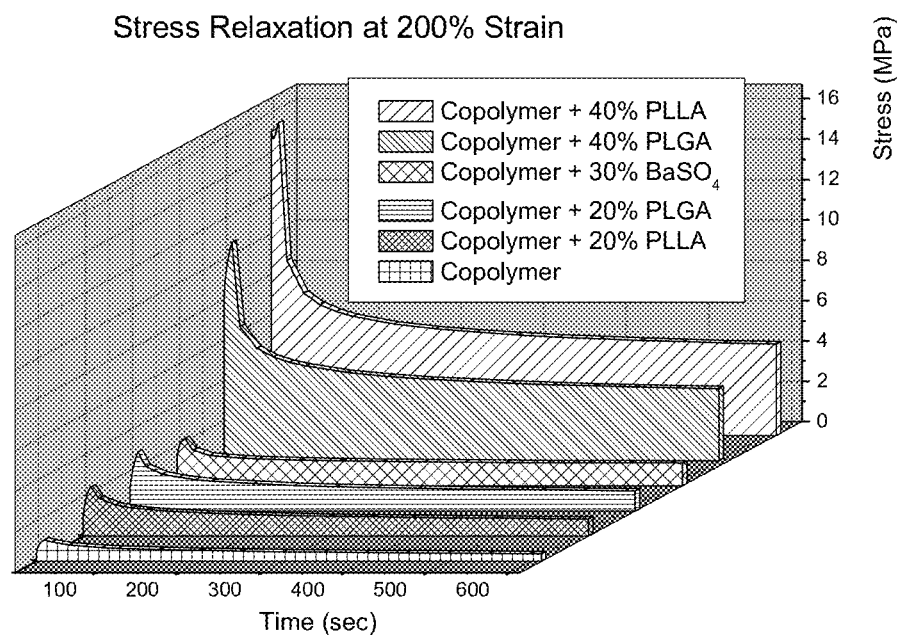

Stress relaxation tests were also conducted at 37° C. to study the polymer's mechanical behavior under constant strain. The sample was rapidly stretched to the required length (100% and 200% elongation) and maintained for 10 min, with the stress recorded as a function of time. The test results are shown in FIG. 15. The results denote that the PLA-PCL copolymer has the least amount of stress relaxation during the test period, while PLA blended copolymer shows the greatest percentage of stress relieved within the first 100 seconds of experiments. So the pure PLA-PCL copolymer resembles an elastomer mechanically among all the candidate polymers, for its low Young's modulus and long relaxation time.

Example 6

In Vitro Deployment Test

Figure 16:
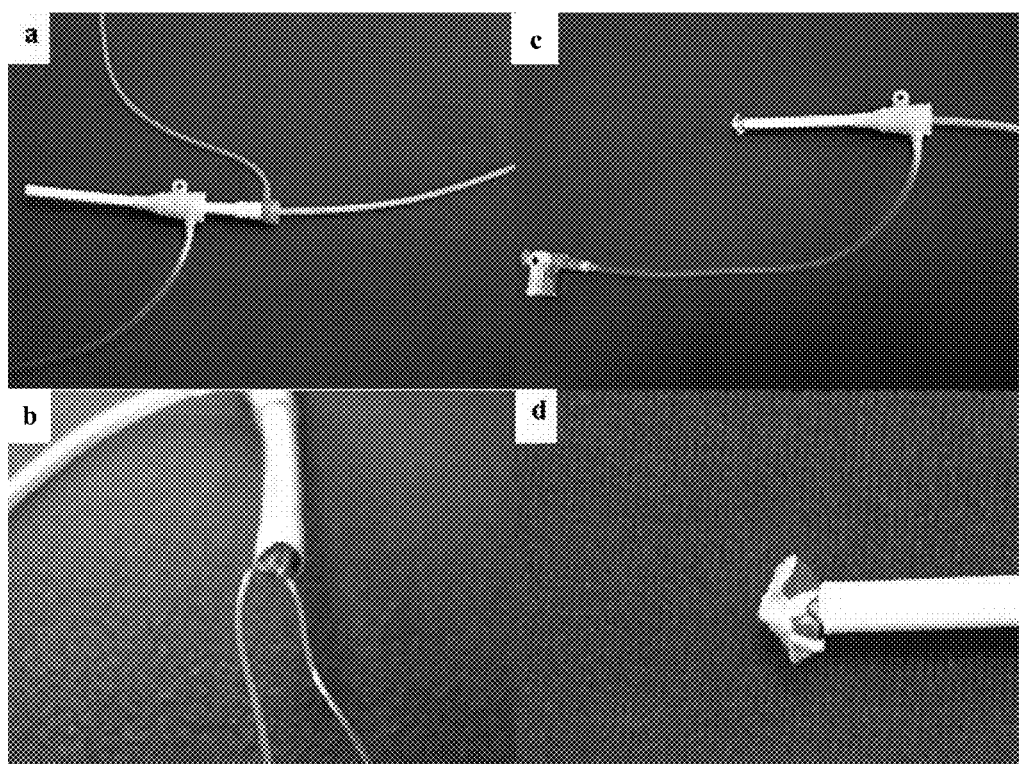
FIGS. 16 a-d show several steps of a test of the deployment procedure of an occlusion device as described herein.

The occlusion device was inserted as its ready-to-be-deployed profile into a sheath of a catheter as described beforehand (FIG. 16*a*). The front end of the LA disc was ensured to be at the tip of the 11F sheath (FIG. 16*b*). In this Figure the loading wire is seen, which is then removed by pulling at one end of it. Then the LA disc was pushed out using the deployment tube attached to the RA disc (FIGS. 16*c* and *d*). The deployment tube was then pulled back slightly to allow tender pulling of the retrieval wire for LA disc to anchor on the septum model. When the operator felt enough anchoring, the RA disc was also released by pushing the deployment tube further. The deployment tube was then retrieved completely and the retrieval wire was cut and withdrawn. The occlusion device was considered to anchor more sufficiently and gave better operating feedback on anchoring, owing to its strengthened spoke-joint structure.

However, for septa thinner than 1 mm, the occlusion device shown in this embodiment leaves considerable amount of gap between the umbrella discs and the septum, giving rise to potential hazard for thrombus formation in the gap. For holes larger than Ø 15 mm, the gap also means an unstable positioning which may result in minor residue shunting. Alternative occlusion devices as described herein can solve these problems by slightly modifying the elasticity, the cross section or the length of the waist portion. Alternatively, the disc-shape can be modified such that the support structures hold the occlusion device in position.

Example 7

In Vitro Deployment Test at a ASD/PFO Model

Figure 17:
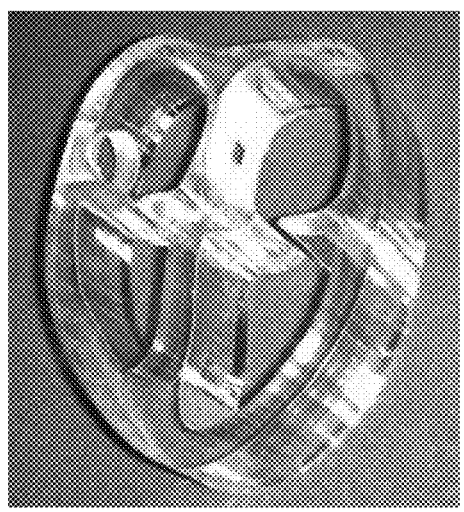
FIG. 17 shows an atrial septal defect/patent foramen ovale (ASD/PFO) model for in vitro deployment tests.

This test aims to verify the deployment and sealing mechanism of the design based on a polycarbonate (PC) septal defect model which is shown in FIG. 17. The in vitro ASD/PFO model has two holes of Ø16 mm on the right atrium wall and atrial septum, respectively. The former provides access for the device to the right atrium; and the latter as the base for a thin copolymer film (200 µm) with a 5×5 mm window as the ASD/PFO model.

The occlusion device of the first aspect was first inserted into an 11F sheath, which went through the right atrial wall of the ASD/PFO model (FIG. 18*a*). Afterwards the front part of the occlusion device comprising the proximal support structure and the proximal occlusion film (LA disc) was pushed out of the sheath and allowed to unfold in the left atrium. The unfolded LA disc was then anchored against the front side of the opening by pulling back the retrieval wire and sat against the septum model. The remaining part of the device was also released from the sheath and unfolded in the right atrium.

After the delivering system retrieval, the occlusion device was positioned well at the defect location as shown in FIG. 18*b*. The photo shows a good sealing result from the right atrium side as well as from the left atrium side.

Radiopacity Test

X-ray visibility of the occlusion device of the first aspect was tested on a fluoroscope (GE, Innova) at National University Hospital, Singapore. A standard acrylic plate (8 mm thickness) plus a slice of pork (with skin and fat on, about 5 cm thick) were used as the phantom on top of the PC ASD/PFO model. A normal examination procedure was performed and X-ray videos/images were taken.

The occlusion device showed remarkable radiopacity even when being covered by two layers of phantom and inside the sheath. Clear device profiles have been captured under the X-ray, owing to high loadings of $BaSO_4$ (40%) at the occlusion device's tip (proximal and distal support structures) and the waist portion. Good X-ray visibility ensures good maneuverability during deployment.

Figure 18:
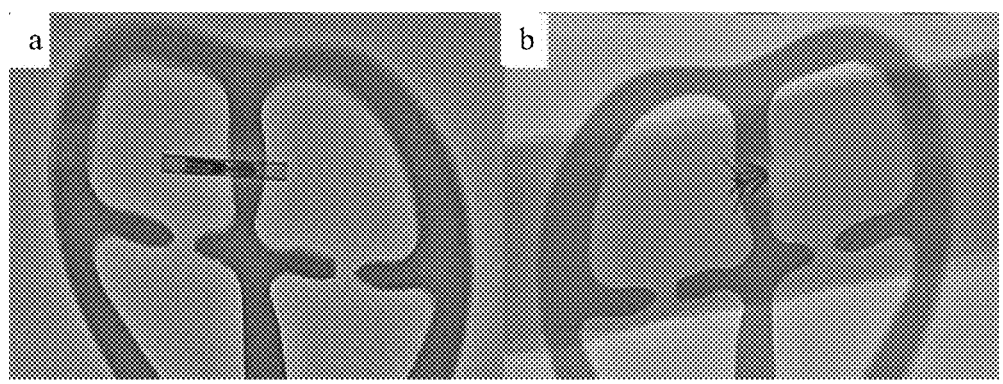
FIGS. 18 a and b show X-ray images of an embodiment of an occlusion device as described herein in sheath (FIG. 18a) and unfolded to the working structure (FIG. 18b) shown on the ASD/PFO model shown in FIG. 17.

FIG. 18 shows the X-ray images of the occlusion device of the first aspect. In FIG. 22*a* the occlusion device is in the sheath which is already placed in the hole of the model. FIG.

18b shows the occlusion device which is deployed in the left atrium and the right atrium, thereby closing the opening from both sides side.

Example 8

In Vivo Tests

Animal Selection

The animals selected were male Yorkshire swines, approximately 50-60 kg weight, because of the similar heart size to humans. The animals were from Innoheart Pte Ltd, a pre-clinical contract research organization in Singapore. The study protocol was approved by the IACUC of Innoheart Pte Ltd. Two occlusion devices according to the first aspect of the application were tested at two animals, namely occluder "DU2" and "DU3". DU stands for Double Umbrella design occluder because the unfolded structure of each disc portion looks like an umbrella.

Creation of ASD/PFO Model

Pre-Medication Administration

The animals were kept for at least two days before the procedure at the facility and pre-medicated with Aspirin (400 mg) 3 days prior to surgery. They were also fasted overnight from 6 pm one day before surgery.

Surgical Preparation

The animals were sedated with 0.5 mg/kg IM TKX cocktail. After sedation, they were brought to the animal preparation room where an IV drip line was inserted into one ear vein and they were then intubated. The surgical site was shaved with electrical shaver and was cleaned with wet gauze and hibiscrub. The animals were placed on the ventilator throughout the duration of the surgery.

Surgical Procedure

Antibiotics (Ampicillin 10 mg/kg) was administered IM at the start of the procedure. ECG, heart rate, respiratory rate, transcutaneous oxygen saturation, tidal volume, and end-tidal $CO_2$ were monitored throughout the procedure. For cardiac catheterization of femoral artery, the femoral artery was exposed through an incision made on the inner thigh. The muscle layers were carefully separated until the femoral artery was exposed. The distal portion of the artery was ligated and a 7F sheath was inserted into the vessel. A proximal ligature was made to secure the sheath. The sheath advanced into the aorta, following which a bolus of heparin were injected.

For atrial access, the second and third ribs were identified and an incision was made. The right atrium of the heart (30) was exposed. A purse-string suture (31) was made before atrial puncture to secure hemostasis after insertion of an 11F sheath (32) as shown in FIG. 19.

Figure 19:
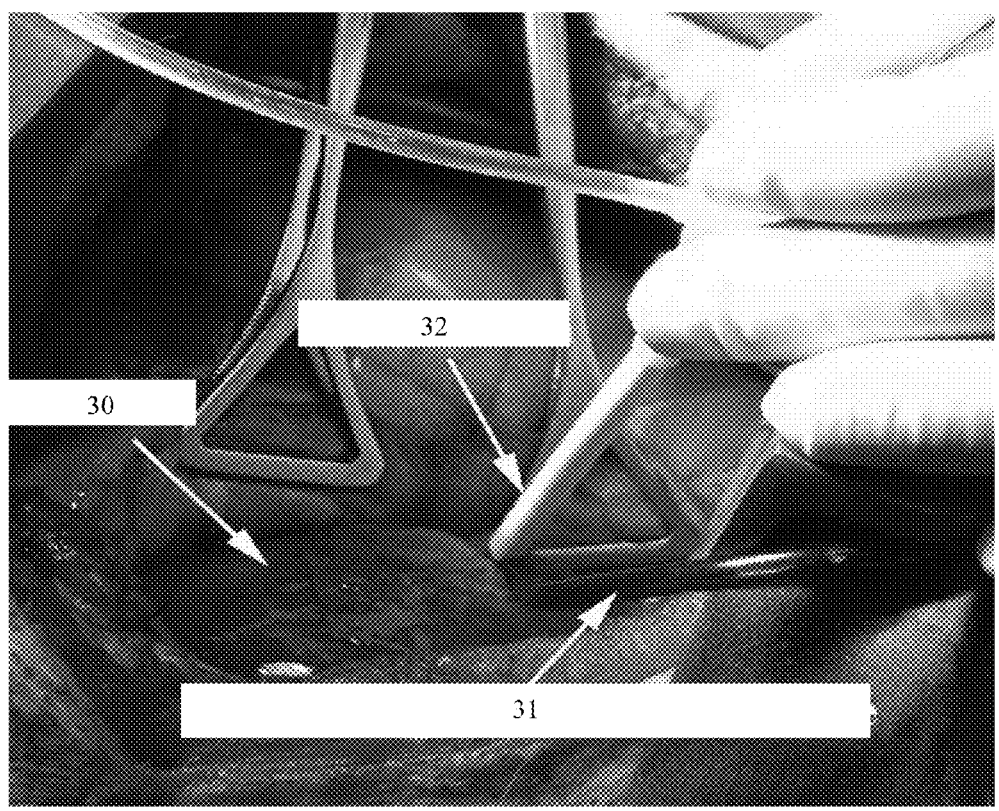
FIG. 19 shows a photo of a puncture of the right atrial wall of a Yorkshire swine during surgery.

The right atrium wall was punctured by a dilator of an 11F sheath, followed by the sheath (32) as shown in FIG. 19. After the sheath went into the right atrium, contrast media was injected to confirm the location of atrial septum, which was then punctured by a long puncture needle. The needle was moved forward careful to avoid free wall puncture and/or aortic puncture. The dilator of the 11F sheath was then gently advanced, after which the needle was removed and a guide wire was introduced into the left atrium. The PFO model was then created by pushing the 11F sheath across the septum, therefore estimated size of PFO was about 4.0 mm. After confirmation of the PFO model on fluoroscopy (FIG. 20), the guidewire and dilator were retrieved, leaving the 11F sheath at the location of created PFO for the occluder deployment.

Operational Procedure and Results

Device Preloading

The occlusion device and delivery system were firstly taken out of the sterilized package and immersed in saline solution. After checking the structure integrity of the device, the surfaces of the occlusion films and the waist portion were flushed continuously using a syringe in the saline until bubbles attached were completely removed. The 9F sheath was also flushed in the saline solution. Using the loading wire inserted in the guide tube, the occlusion device was loaded into the 9F sheath. Then the occlusion device was pulled by the loading wire till the tip of the LA disc (proximal support structure and proximal occlusion film) was seen at the distal end of the 9F sheath. The loading wire was removed from the LA disc. The deployment tube with retrieval wire in it followed the occlusion device entered into the 9F sheath. The sheath and device in it were flushed again using the syringe.

Device Deployment

Figure 20:
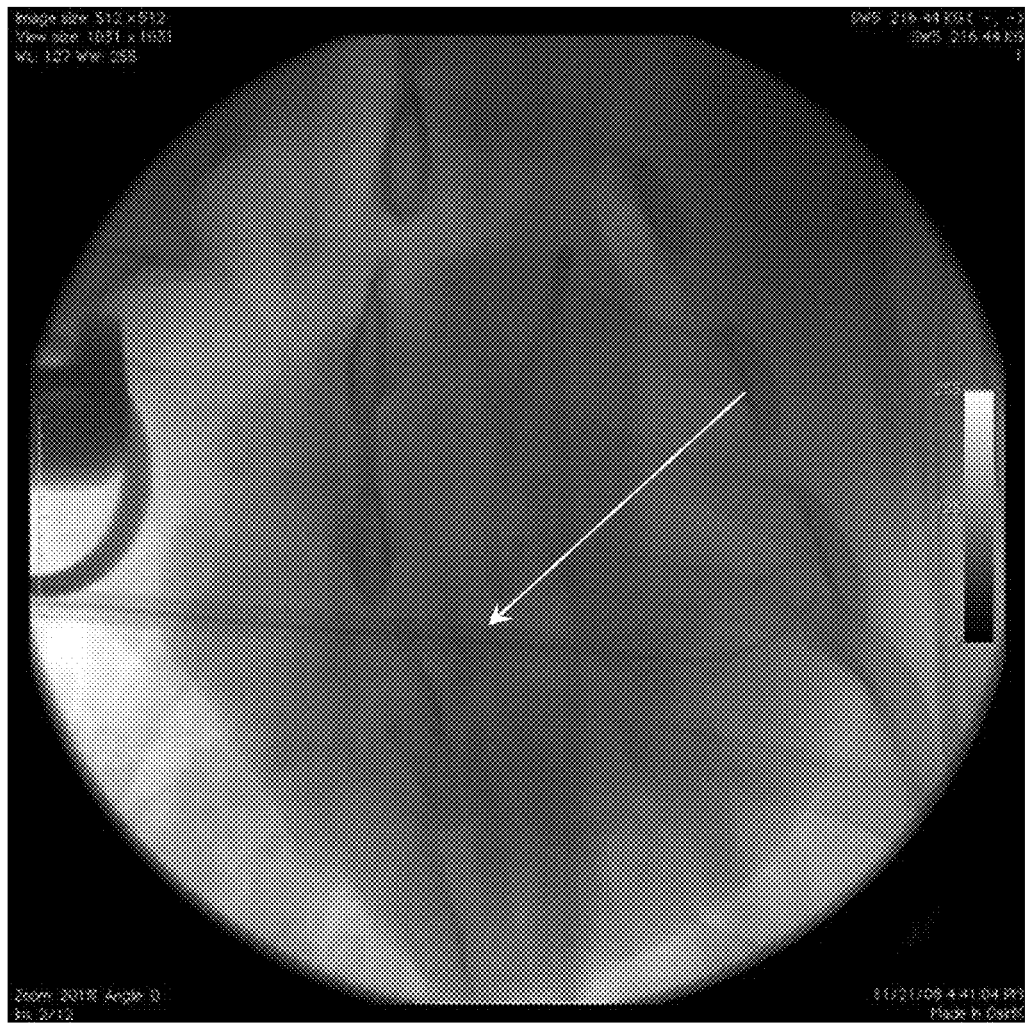
FIG. 20 shows an X-ray image of the 11F sheath (the arrow indicates the 11F sheath across created septal defect) used to deploy the occlusion device across the created septal defect in the Yorkshire swine taken under fluoroscope.

Following the above pre-surgical loading, the 9F sheath was taken out from the saline solution and inserted directly into the 11F sheath which had been positioned previously across the ASD/PFO model (FIGS. 19 and 20). The occlusion device was then pushed by the deployment tube into the 11F sheath from the 9F sheath and then the 9F sheath was removed.

Figure 21:
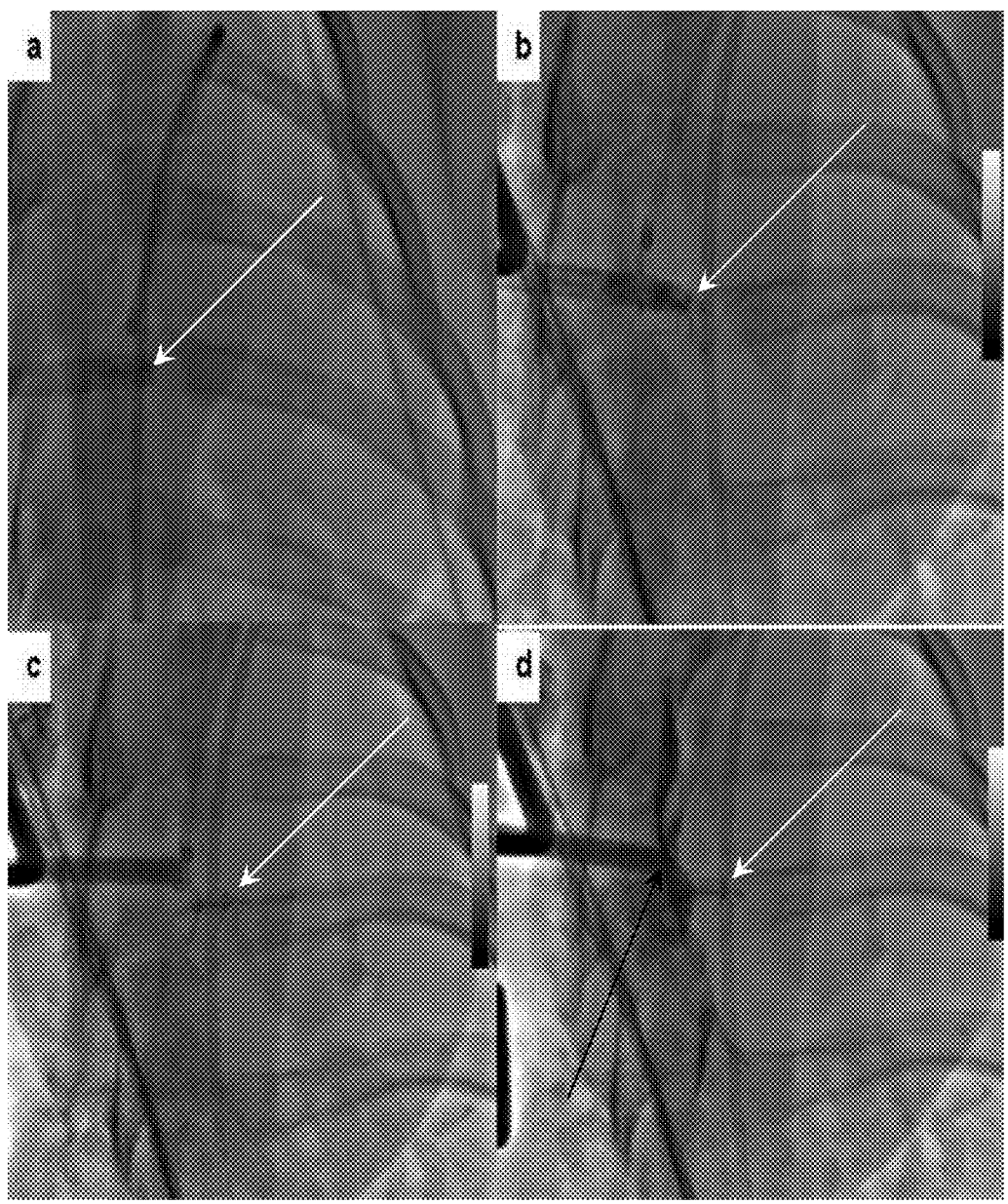
FIGS. 21 a-d show fluoroscopy images of the deployment procedure of an embodiment of an occlusion device of the present invention: (a) device in sheath (the arrow indicates the tip of the occlusion device in the sheath), sheath advanced across the created septal defect into the left atrium; (b) proximal support structure advanced out of the sheath, anchoring against the septum (the arrow indicates the occlusion device anchoring); (c) full occlusion device deployed (see arrow) and sheath withdrawn; and (d) deployment finished (white arrow indicates the occlusion device position), radioopaque contrast injection demonstrated no leak (contrast injection is indicated by the black arrow).

Under the fluoroscopic guidance, the device was pushed forward in the 11F sheath until LA disc was released from the sheath and in the left atrium (FIG. 21a). The deployment was paused for 5 seconds to allow the LA disc to unfold, the device was then pulled back and anchored against the atrial septum by withdrawing the retrieval wire in the deployment tube, during which resistance can be sensed manually and the position monitored under fluoroscopy (injected contrast medium) (FIG. 21b). With tension on the deployment tube (ensuring no device movement), the sheath was withdrawn until the RA disc was released in the right atrium. A gentle "to and fro" motion on the retrieval wire assured a secure position across the PFO model, which was also displayed under fluoroscopy (FIG. 21c).

For "DU3", the 11F sheath had once gone too deep into the left atrium where the entire device had accidentally been released. Therefore the device ("DU3") was retrieved in the following steps by holding the retrieval wire in the deployment tube and then pushing the 11F sheath forward to force the device into the sheath. The device was then pulled out of the sheath and was replaced by another new device in a new 9F sheath for repeating the deployment procedure. In the example of "DU2", this step was not necessary, because the deployment was satisfactory.

When the deployment was satisfactory, the retrieval wire was removed by pulling it out of the 11F sheath and was withdrawn followed by the removal of the deployment tube. The final fluoroscopic result is shown in FIG. 21d with no leak across the septum.

After the device deployment, the animals were allowed to recover as per protocol. Painkiller (Ketorolac 1 mg/kg) was administered IM.

One Month Follow-Up and Sacrifice

Figure 22:
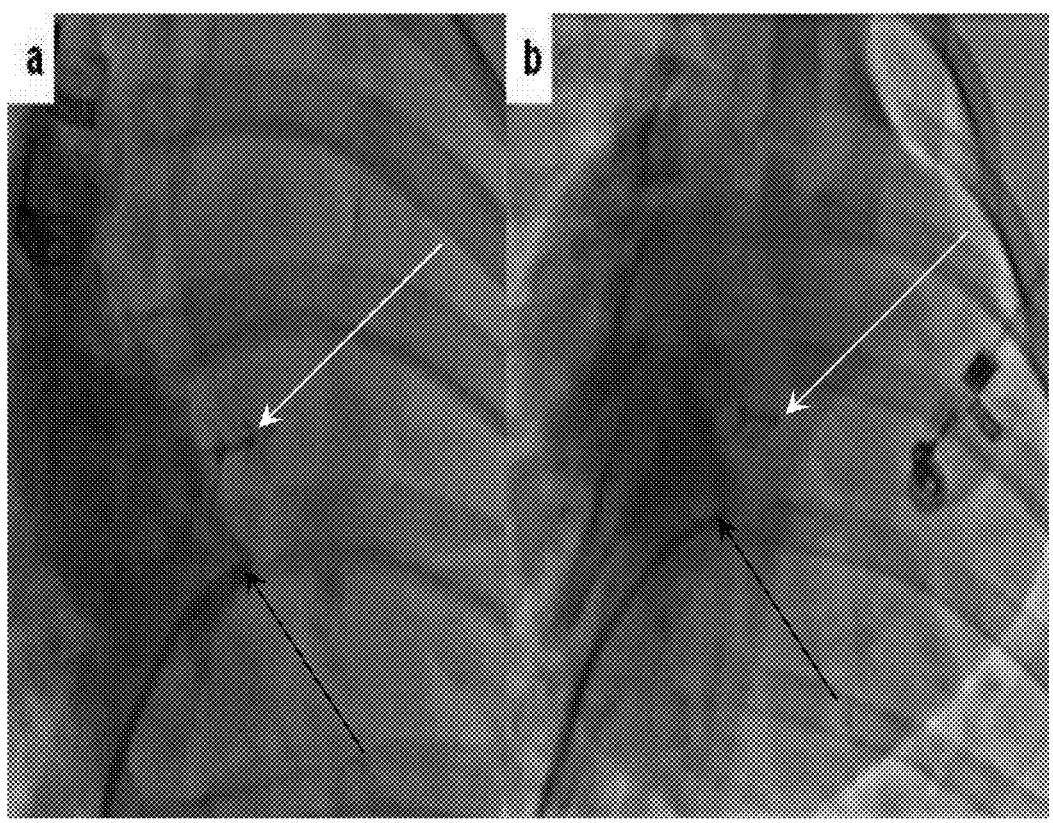
FIGS. 22 a and b show fluoroscopic tests of two embodiments of occlusion devices of the present invention after one month: (a) occlusion device "DU2" (white arrow indicates the occlusion device position), radioopaque contract injection demonstrated no leak (contrast injection is indicated by the black arrow); and (b) occlusion device "DU3" (white arrow indicates the occlusion device position), radioopaque contract injection demonstrated no leak (contrast injection is indicated by the black arrow).

After a month of follow up, both animals were well and gained weight. Before sacrifice, the animals were anaesthetized and the device position and leakage was checked by fluoroscopy and contrast injection in the left atrium. Residual shunting was also assessed by transthoracic echocardiography (TTE) in combination with an agitated saline contrast medium injection (bubble test). FIG. 22 shows that both devices were intact and the PFO models were well sealed.

FIG. 22a shows the fluoroscopic test of "DU2" after one month and FIG. 22b shows the same for "DU3".

Figure 23:
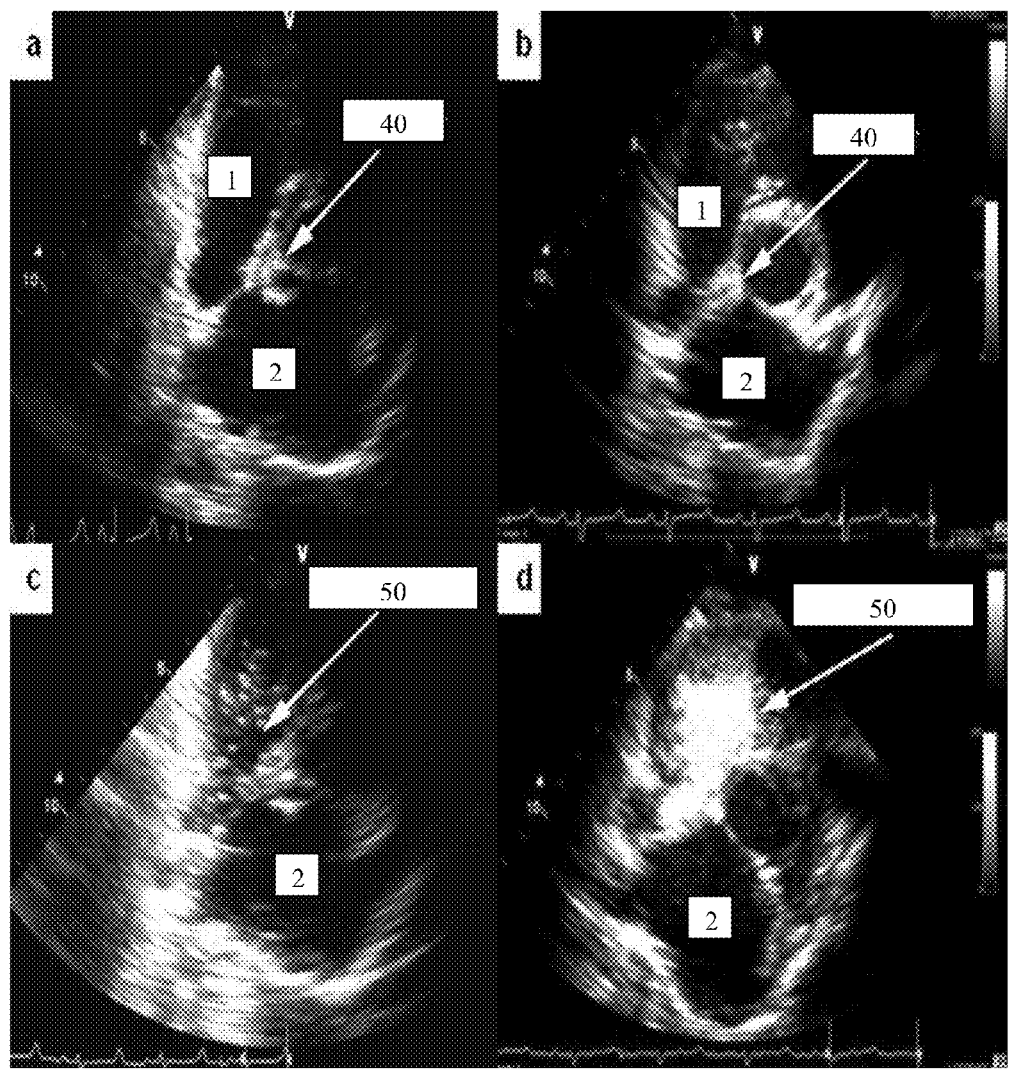
FIGS. 23 a-d show transthoracic echiocardiography (TTE) images of the TTE bubble test of the occlusion devices "DU2" and "DU3": TTE image after one month's implantation for "DU2" (a) and "DU3" (b), respectively; bubbles in the right atrium (RA) for "DU2" (c) and "DU3" (d), respectively.

The echo test results are shown in FIG. 23. Both "DU2" and "DU3" (40) can be seen clearly under TTE (FIG. 23a and FIG. 23b, respectively). When contrast medium was injected, dense bubbles (50) were seen in the right atrium (1), and no bubble was found in the left atrium (2), proving no right-to-left shunting (FIG. 23c for "DU2" and FIG. 23d for "DU3").

Device Macroscopic and Histological Examination

After a lethal injection of euthanasia solution Valabarb, complete autopsy was performed in both animals. The hearts and adjacent vessels were explanted and reviewed for the gross appearance of the device.

Macroscopic Examination Results

Figure 24:
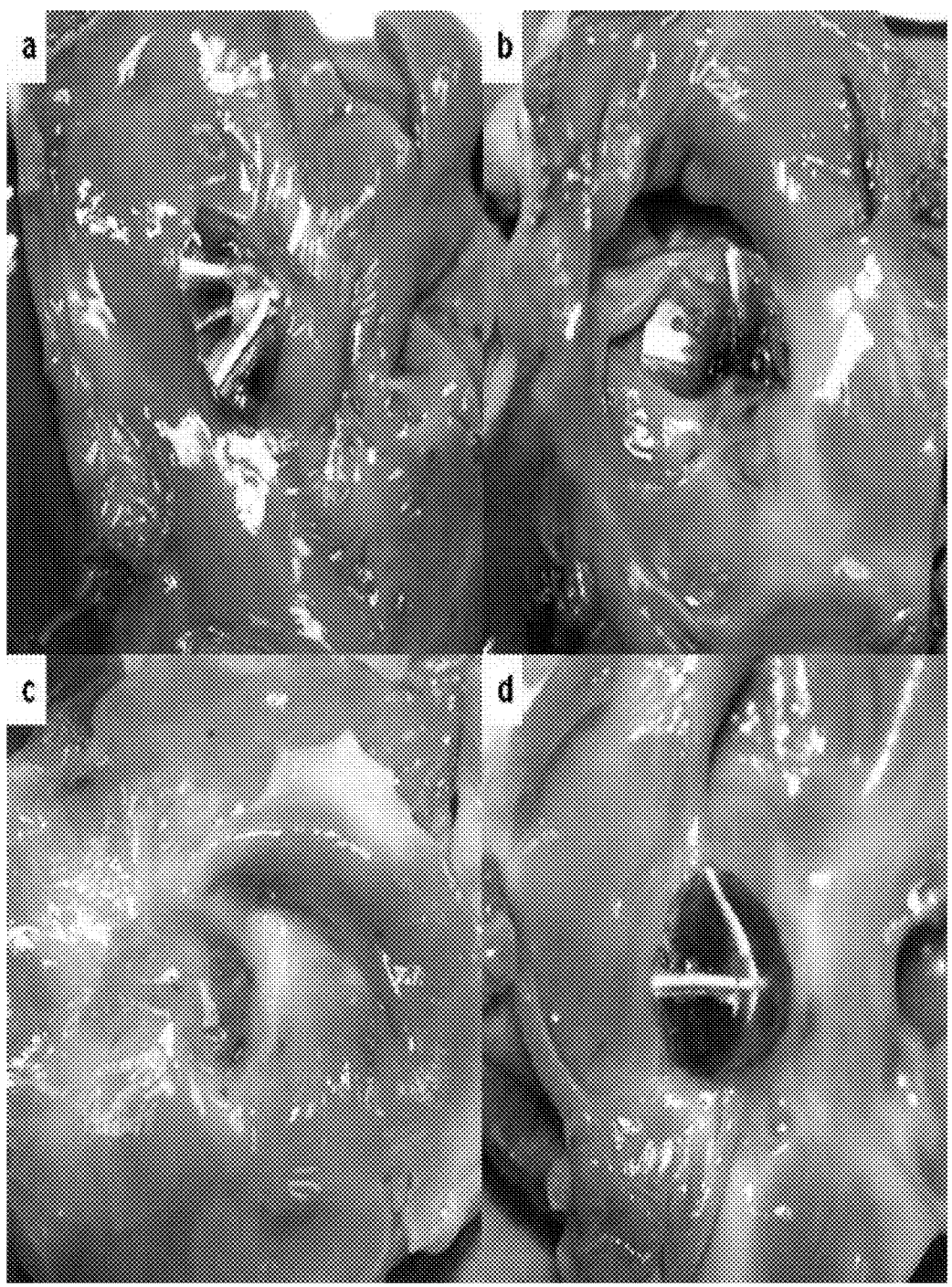
FIGS. 24 a-d show a macroscopic examination of occlusion devices implanted: (a) RA disc of "DU2" the right atrium (RA); (b) LA disc of "DU2" in the left atrium (LA); (c) RA disc of "DU3" in the right atrium (RA); and (d) LA disc of "DU3" in the left atrium (LA).

The gross pathology for "DU2" and "DU3" is shown by macroscopic examination of the occlusion devices implanted: FIG. 24a shows the RA disc of "DU2"; FIG. 24b shows the LA disc of "DU2"; FIG. 24c shows the RA disc of "DU3"; and FIG. 24d shows LA disc of "DU3".

Both devices were intact and there were no fractures or damages of the spokes. For "DU2", halves of both RA and LA discs are covered and gap is seen between each of the other halves and septum (FIGS. 24a & b). Some thrombi can be seen in such gaps. For "DU3", the RA disc has been completely covered by a thick glistening surface layer (FIG. 3c); however, the gap between the LA disc and the septum is filled with thrombi and only one quarter of the LA disc is covered by endothelial tissue.

Histological Examination

After macroscopic examination, the septum tissues with devices were fixed in alcoholic formaldehyde for 72 hours. The histological sections were taken from the right and left atrial wall having the device and septal myocardium. Tissue samples were embedded in paraffin wax, serially sectioned, and stained with hematoxylin and eosin.

Figure 25:
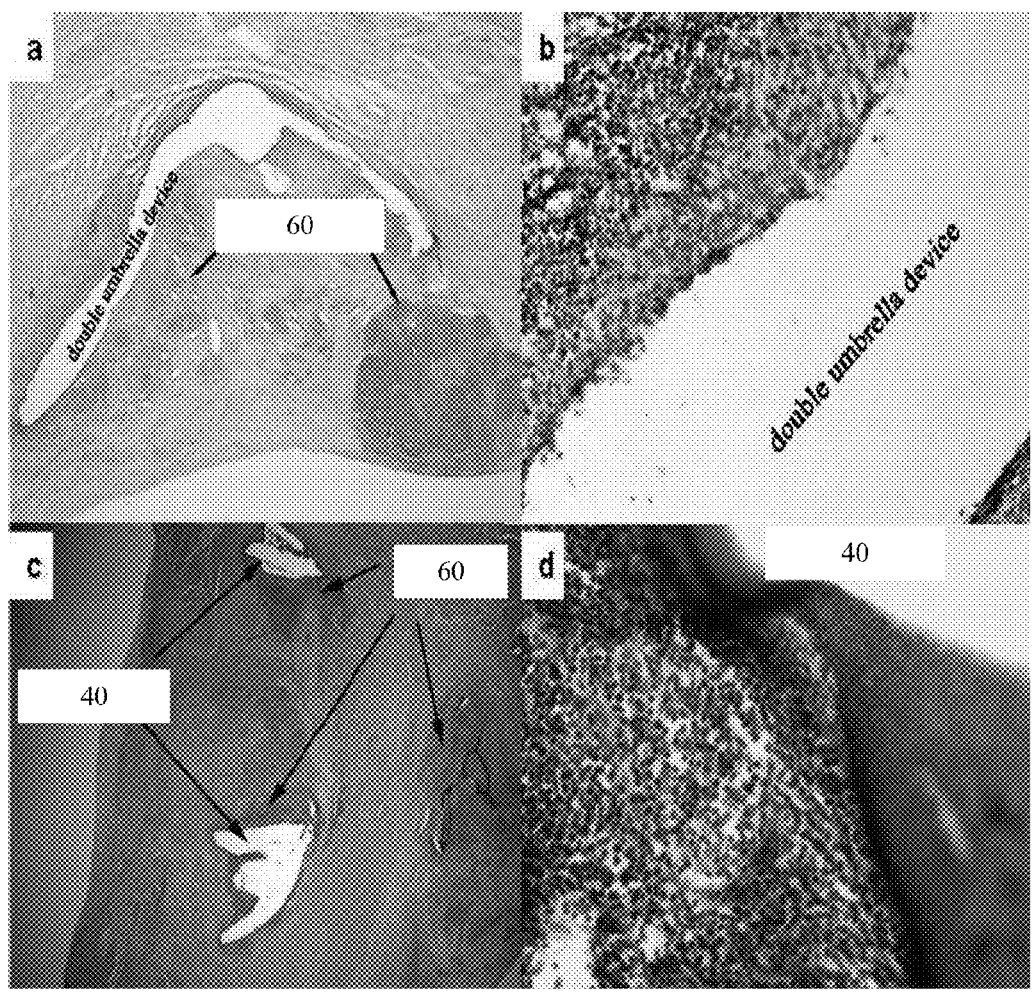
FIGS. 25 a-d show the histology of the healing response to the "DU2" (a and b) and "DU3" (c and d) occlusion devices as described herein.

The healing response of occlusion devices of the first aspect after one month in vivo test is shown in FIGS. 25a and b for "DU2" and in FIGS. 25c and d for "DU3". It can be seen that the occlusion devices (40) stimulated moderate growth of inflammatory cells (60). The higher magnification shows that the inflammatory cells were densely layered close to the devices. For "DU3", there were some signs of bleeding.

Degradation Examination of the Films

Microscopic Examination

Figure 26:
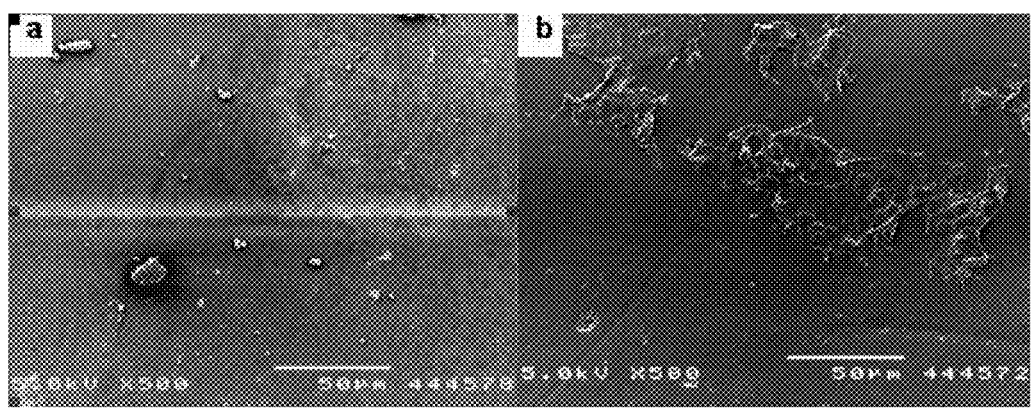
FIGS. 26 a and b show photos of scanning electron microscopy (SEM) observation of the starting film (FIG. 26a) and of the film explanted after one month (FIG. 26b) of an embodiment of the occlusion device as described herein.

A tiny piece, of film was cut from the explanted LA disc of the "DU2" occlusion device after sacrificing the swine. It was cleaned with ethanol followed by distilled water in an ultrasonic bath. Scanning electron microscope (SEM) examination was conducted thereafter for the explanted film with an original starting film as control. FIG. 26 shows that the starting film surface was smother (FIG. 26a). The film surface after one month implantation was rough and had a number of crumples, mostly due to the hot pressing process. Pore formation was also observed and is considered a result of degradation (FIG. 26b).

Molecular Weight Test

Figure 27:
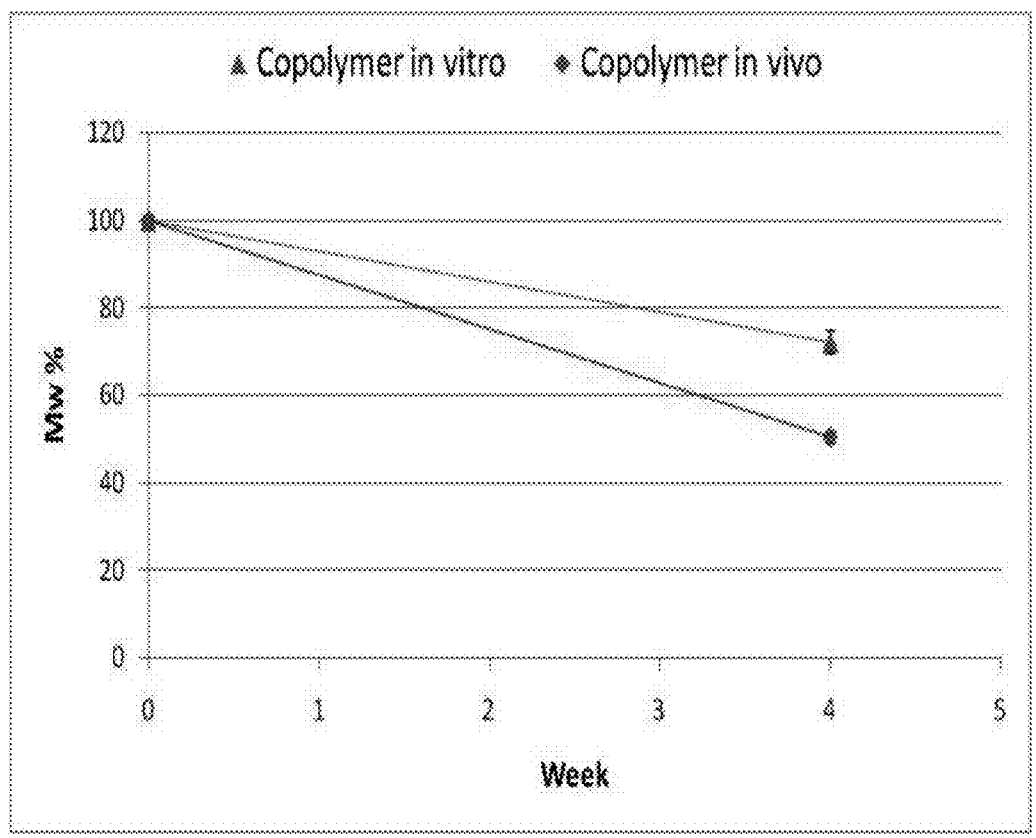
FIG. 27 shows the results of a copolymer degradation test in vitro and in vivo.
Figure 28:
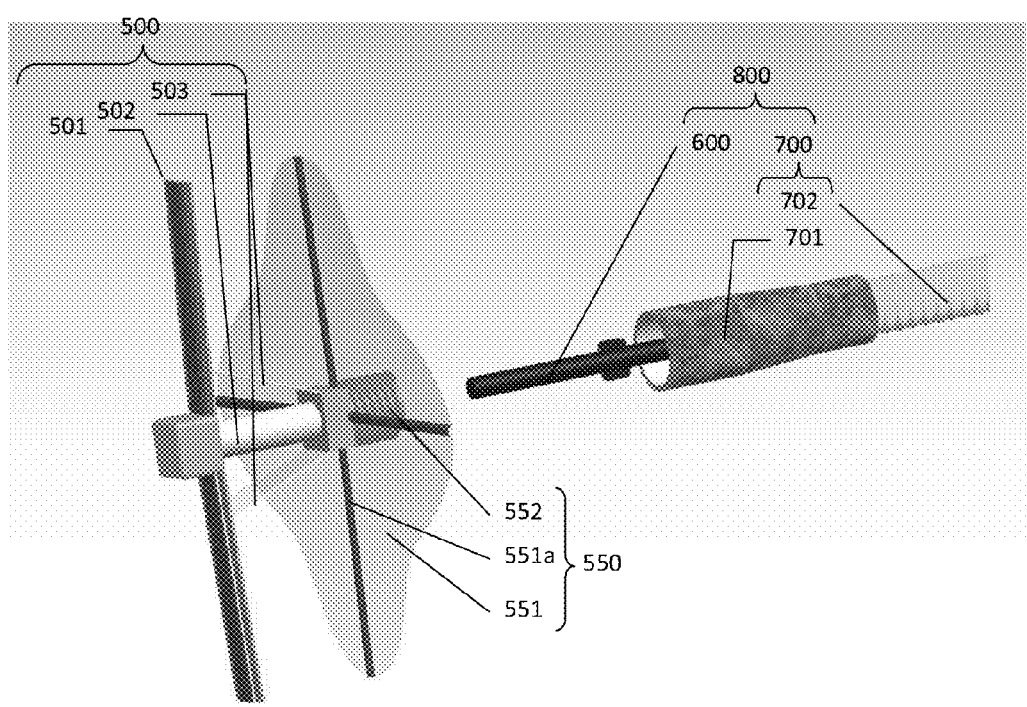
FIG. 28 shows an exploded perspective view of components of the occlusion device according to the second aspect of the invention including parts of the delivering system of the occlusion device.

The Molecular weight (Mw) of the sample film explanted from "DU2" was measured on GPC and compared with the in vitro degradation result at week 4 (FIG. 27). As expected, in vivo degradation is faster (week 4) for the copolymer, comparable to degradation for the copolymer in vitro (week 8). This is mostly due to a harsher degradation environment in vivo.

Example 9

In FIGS. 28 to 33, a particular embodiment of an occlusion device of the second aspect (400) is shown which has been adjusted for the use as an ASD/PFO occluder. The occlusion device of this embodiment comprises a combination of a proximal support structure (501) and a waist portion (502), which are integrally formed (500). The proximal support structure as shown includes two arms (501) comprising spokes and a small strip of an occlusion film. The spokes of the proximal support structure are shown in dark grey wherein the occlusion film is shown in light grey. The two arms integrally formed by laminating the spokes onto the polymer occlusion film are welded to the middle section of the proximal support structure which can be folded in the direction of the waist portion (as shown in FIG. 34b).

Figure 32:
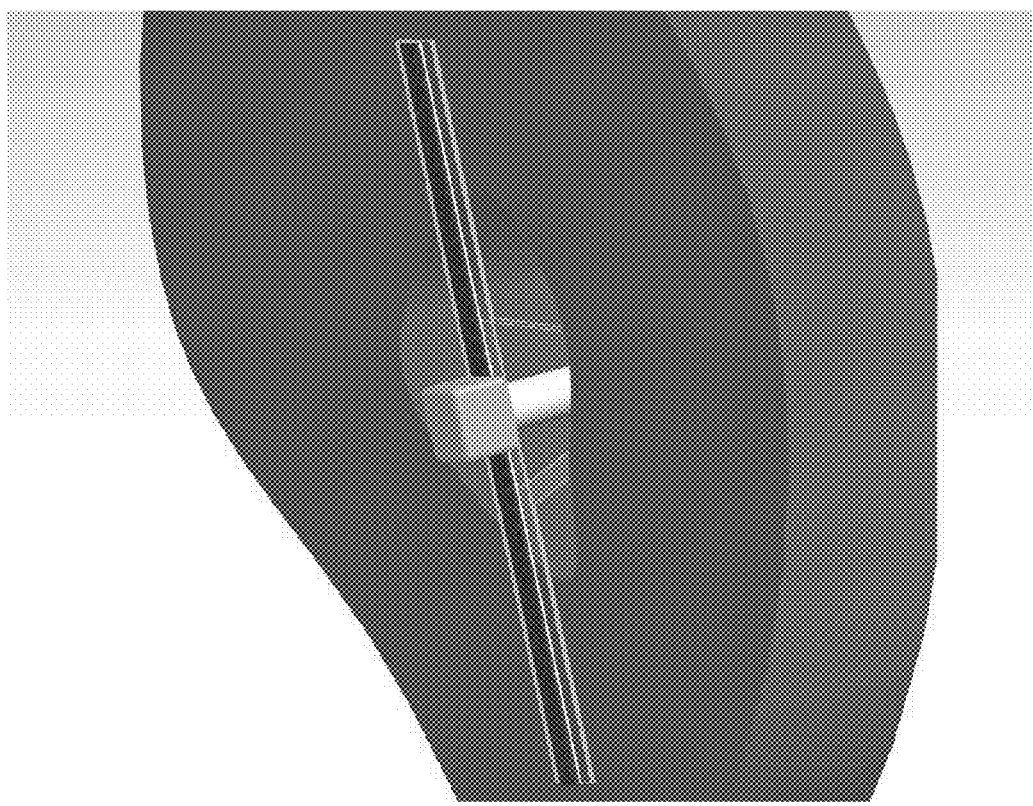
FIG. 32 shows an occlusion device of the second aspect from the proximal side which is deployed at a model of a tissue defect.

The occlusion device of this embodiment further comprises a hollow tube as waist portion (502) connected to the middle section of the proximal support structure. At the other site of the waist portion (502), a means (520) for holding the reinforcing means (503) and for bonding the connector of the distal support structure are provided (as shown din FIG. 30). The reinforcing means are welded at the arms (501) of the proximal support structure at a distance (510) having a maximum of not more than the maximum diameter of the opening of the tissue defect as shown in FIG. 29. After the occlusion device has been anchored at the tissue defect, the waist portion (502) and the reinforcing means (503) are positioned in the opening. The length of the waist portion is adjusted such that the arms of the proximal support structure (501) are anchored at the front side and the arms of the distal support structure (551a) are anchored at the back side of the defect (as shown in FIGS. 32 and 33) to close the tissue defect.

Figure 30:
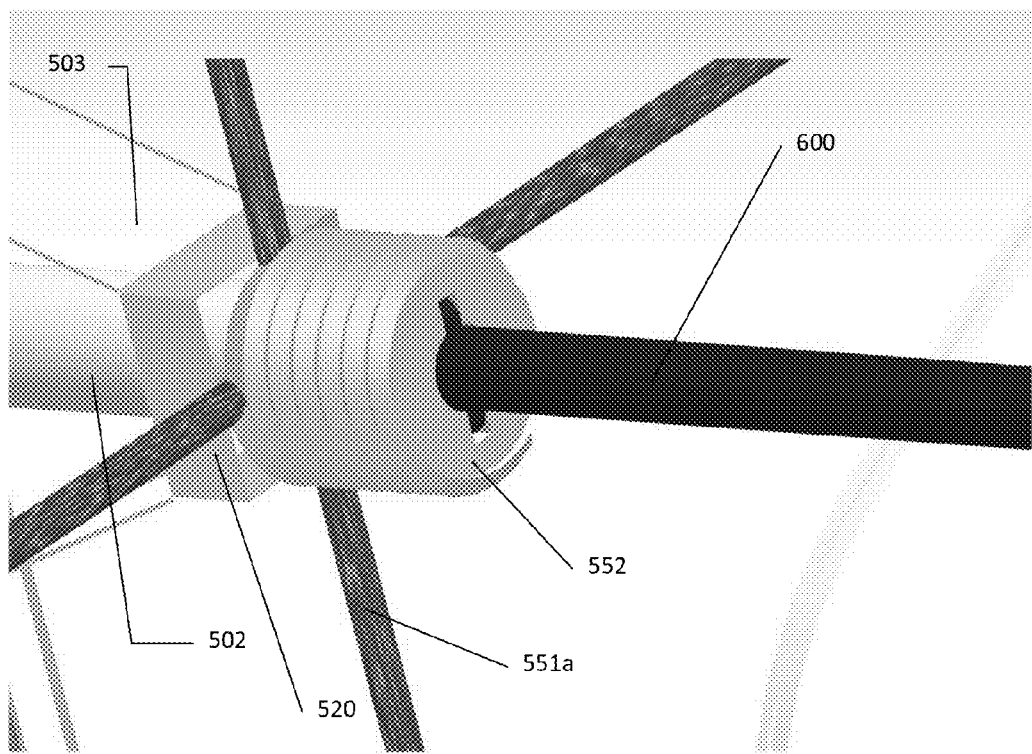
FIG. 30 shows an enlarged perspective view of the rear end of the occlusion device shown in FIG. 28 and, in particular, the rod engaged into the locking member of the distal support structure.
Figure 33:
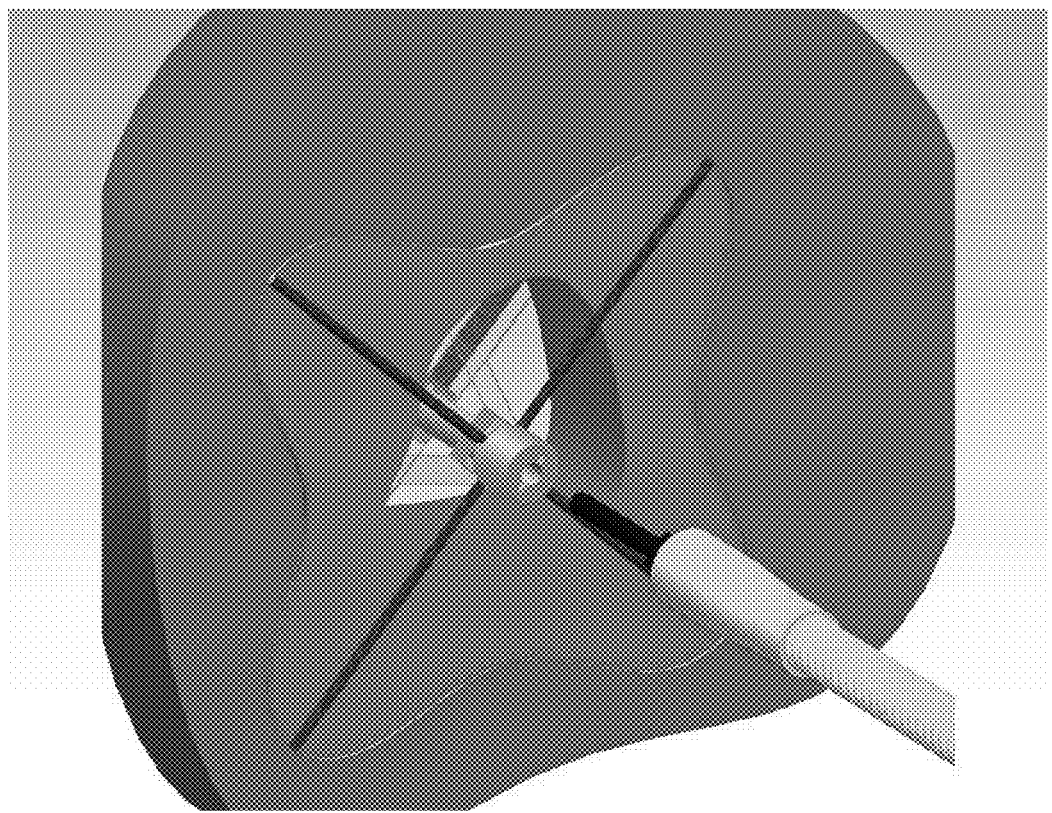
FIG. 33 shows an occlusion device of the second aspect from the back side of the defect which is deployed at a model of a tissue defect, wherein the delivering system is shown in its disconnected state.

The occlusion device of this embodiment has a distal support structure consisting of four spokes (551a) and a distal occlusion film (551) spanned over any of those spokes to form a flower-like distal support structure (as shown in FIG. 33). The distal support structure further comprises a middle section in the form of a hollow tube at which the spokes are welded such that they are foldable. The middle section integrally comprises a hollow tube (552) having a thread at its exterior surface which can be engaged with the hollow connecting member (701) of the second delivering means (700) for connecting the deployment tube (702) to the distal support structure (please see FIG. 28). The connecting member (701) has the same diameter as the hollow tube (552) and has a threaded interior surface (not shown in FIG. 28). The middle section of the distal support further comprises a locking member in which protruding means of the first delivering member (600) can be engaged as it is shown in FIG. 30. Thereby, a rotation of the distal support structure during the deployment process can be avoided and disconnecting the second delivering means by a rotational movement of the connecting member (701) from the distal support structure can be facilitated. The locking mechanism is shown in FIG. 30 in an enlarged view.

Figure 31:
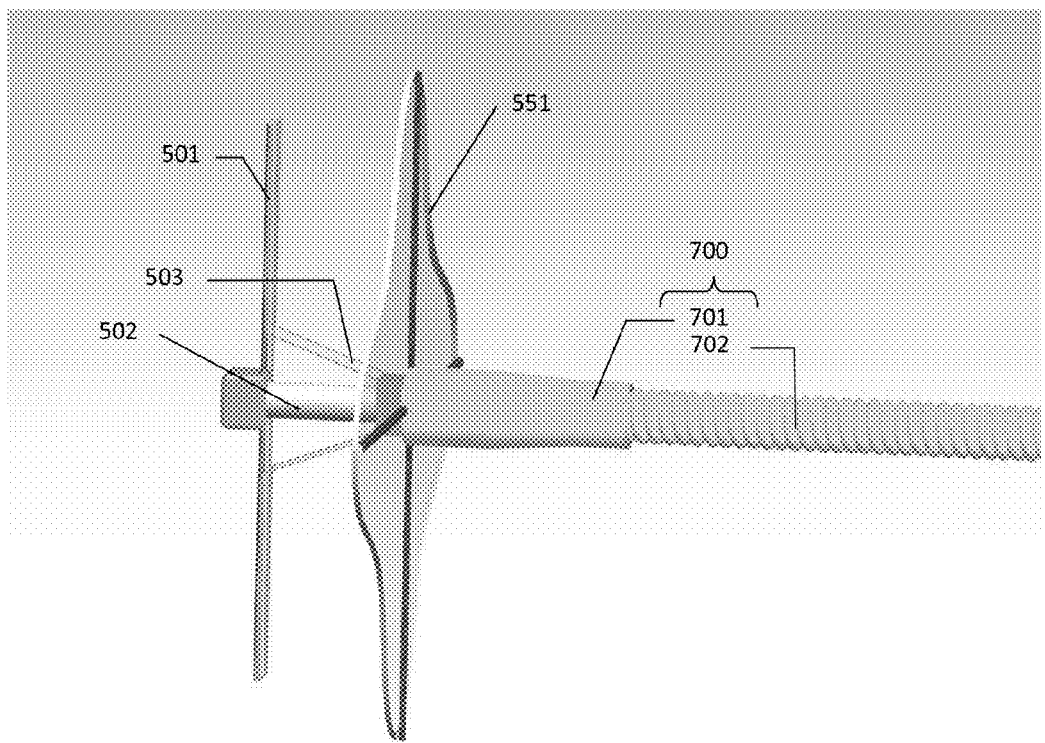
FIG. 31 shows a perspective view of the occlusion device shown in FIG. 28 including the delivery system in an assembled state.

As shown in FIG. 31, the delivering system according to this embodiment of the occlusion device of the second aspect comprises a polymeric wire spring for guiding the second delivering means in the catheter and for being used as rod housing. This means is also used to retrieve the second delivering means after the deployment of the occlusion device.

It is needless to say that this occlusion device can be adjusted and modified by any means and feature as described beforehand for the occlusion devices of the first or second aspects.

The above description and exemplary part of the alternative occlusion device design of the first and second aspects of the application shows that the general concept of the present application to replace the current permanent metallic devices was successful. This has been accomplished by utilizing fully biodegradable materials to provide occlusion devices such as ASD/PFO occluders which show a good healing response. The design of occlusion devices of the first and second aspects also decreases thrombogenicity, increases endothelialization, minimizes the foreign body reactions, and decreases immunological and inflammatory responses compared to conventional double umbrella occluders.

The anchoring and the sealing functions have been successfully achieved with the occlusion device according to the first and second aspects. The specific structural design of the scaffold holds the devices in a satisfactory position and keep them stable as has been shown for the device of the first aspect by the above in vivo tests in animals. The TTE bubble test shows that there are no signs of leakage from the right atria (RA) to the left atria (LA), indicating an adequate sealing of the opening.

The in vitro degradation studies and post-mortem ex-plantation made on the devices of the first aspect confirm that the occlusion devices of the first and second aspects have a good integrity and mechanical strength. Therefore, large defects can be securely sealed with these occlusion devices. Furthermore, the occlusion devices of the first aspect show minor thrombosis and foreign body reaction compared to the current occlusion devices having a metallic structure because the design allows the reduction of the inner structural gaps.

In addition, the method of the third aspect makes it possible to achieve the above-mentioned results with the occlusion device of the first and second aspects. Moreover, the method of the third aspect allows not only an easy deployment of the occlusion device at the correct position but also the retrieval of the occlusion device, if this would be necessary, for example due to an accidental deployment.

The invention claimed is:

1. An occlusion device for closing an anatomical defect in a tissue having an opening connecting a front side and a back side of the tissue, the occlusion device comprising:
    a scaffold that includes:
        a proximal support structure comprising a first middle section, at least two arms extending from the first middle section, and a first connector extending from the first middle section;
        a distal support structure comprising a second middle section, at least two arms extending from the second middle section, and a second connector extending from the second middle section;
        a waist portion configured to extend through the opening of the anatomical defect and connecting the proximal support structure with the distal support structure, the waist portion comprising a hollow tube with a proximal end and a distal end; and
        a proximal occlusion film supported by the proximal support structure and a distal occlusion film supported by the distal support structure, wherein:
        the proximal support structure and the distal support structure are of a polymeric material,
        the proximal support structure has a stiffness higher than a stiffness of the distal support structure,
        the first connector comprises a first hollow joint protruding from the first middle section towards the waist portion,
        the second connector comprises a second hollow joint protruding from the second middle section towards the waist portion,
        the proximal support structure and the distal support structure are detachably connectable to the waist portion such that the first hollow joint of the proximal support structure is configured to be inserted into the proximal end of the hollow tube and the second hollow joint of the distal support structure is configured to be inserted into the distal end of the hollow tube, and
        the first hollow joint of the proximal support structure is integrally provided together with the at least two arms of the proximal support structure and the hollow joint of the distal support structure is integrally provided together with the at least two arms of the distal support structure.

2. The occlusion device according to claim 1, wherein the at least two arms of the proximal support structure are three or more spokes outwardly extending from a middle of the proximal support structure and have respective inner ends connected with each other.

3. The occlusion device according to claim 2, wherein each of the proximal support structure and the distal support structure comprises 2 to 8 of said spokes.

4. The occlusion device according to claim 1, wherein the at least two arms of the distal support structure are three or more spokes outwardly extending from a middle of the distal support structure and have respective inner ends connected with each other.

5. The occlusion device according to claim 1, wherein the at least two arms of the proximal support structure have respective inner ends and are configured to be folded at their inner ends to be insertable into a sheath in either an inward or outward direction and the at least two arms of the distal support structure have respective inner ends and are configured to be folded at their inner ends to be insertable into the sheath in either an inward or outward direction.

6. The occlusion device according to claim 1, wherein the proximal occlusion film expands between the at least two arms of the proximal support structure.

7. The occlusion device according to claim 1, wherein the distal occlusion film expands between the at least two arms of the distal support structure.

8. The occlusion device according to claim 1, wherein one or more elements selected from the proximal support structure, the proximal occlusion film, the distal support structure, the distal occlusion film, and the waist portion comprise a therapeutically active agent.

9. The occlusion device according to claim 8, wherein the therapeutically active agent is selected from the group consisting of a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, and an anti-hypertensive agent.

10. The occlusion device according to claim 1, wherein one or more of the proximal support structure, the proximal occlusion film, the distal support structure, the distal occlusion film, and the waist portion comprise a radiopacifier.

11. The occlusion device according to claim 1, further comprising a delivering system comprising:
    a sheath; and
    at least one first delivering member configured to move the scaffold through the sheath.

12. The occlusion device according to claim 11, wherein the at least one first delivering member is a loading wire removably connected to the proximal support structure.

13. The occlusion device according to claim 12, wherein the loading wire forms a loop running through the proximal support structure.

14. The occlusion device according to claim 12, further comprising a guide tube adapted to house the loading wire and to guide the loading wire through the sheath.

15. The occlusion device according to claim 11, further comprising a second delivering member configured to move the scaffold by pushing it at the distal support structure through the sheath.

16. The occlusion device according to claim 11, further comprising a retrieval wire removably connected to the distal support structure.

17. The occlusion device according to claim 16, wherein the retrieval wire forms a loop running through the distal support structure.

18. The occlusion device according to claim 17, wherein the retrieval wire is adapted to be removed by pulling at one end of the retrieval wire.

19. The occlusion device according to claim 1, wherein the waist portion is a polymeric tube.

20. The occlusion device according to claim 1, wherein the entire occlusion device is made of the polymeric material.

21. The occlusion device according to claim 20, wherein the polymeric material comprises a non-biodegradable polymer selected from the group consisting of polyurethane, poly (ether urethanes), poly(ester urethanes), polyvinylchloride, polyalkylenes, polyethylene terephthalate, polyvinylacetate, poly ethylene-co-vinyl acetate and nylon.

22. The occlusion device according to claim 20, wherein the polymeric material comprises a biodegradable polymer selected from the group consisting of polycaprolactone (PCL), polylactic acid (PLA), polycaprolactone-polylactic acid copolymer (PCL-PLA copolymer), polyglycolide (PGA), poly-L-lactide (PLLA), poly-D-lactide (PDLA), polylactide-polyglycolide copolymer (PLGA), polylactic acid-polyethylene oxide copolymers, polygluconate polyhydroxybutyrate, polyanhydride, polyphosphoester, poly (amino acids), polydioxanone, cellulose, collagen and chitosan.

23. The occlusion device according to claim 22, wherein the polymeric material of the proximal support structure has a higher Young modulus than the polymeric material of the distal support structure.

24. The occlusion device according to claim 23, wherein the polymeric material of the proximal support structure has a modulus range of about $10^7$ to about $10^9$ Pa at 37° C.

25. The occlusion device according to claim 23, wherein the polymeric material of the distal support structure has a modulus range of about $10^5$ to about $10^7$ Pa at 37° C.

26. The occlusion device according to claim 1, wherein the proximal support structure, the distal support structure and the waist portion comprise a radiopacifier.

27. The occlusion device according to claim 15, wherein the second delivering member is a deployment tube.

28. The occlusion device according to claim 1 provided in a sterilized package.

29. The occlusion device according to claim 1, wherein said waist portion extends along a longitudinal axis and the at least two arms of the proximal support structure and/or the at least two arms of the distal support structure are angled towards the waist portion such that angles formed between each of the at least two arms of the proximal support structure and the longitudinal axis and/or each of the at least two arms of the distal support structure and the longitudinal axis are acute.

30. An occlusion device for closing an anatomical defect in a tissue having an opening connecting a front side and a back side of the tissue, the occlusion device comprising:
a scaffold that includes:
 a proximal support structure comprising a first middle section, at least two arms extending from the first middle section, a first connector extending from the first middle section, and a proximal occlusion film supported by the proximal support structure;
 a distal support structure comprising a second middle section, at least three arms extending from the second middle section, a second connector extending from the second middle section, and a distal occlusion film supported by at least two of the at least three arms; and
 a waist portion adapted for extending through the opening of the anatomical defect and connecting the proximal support structure with the distal support structure, the waist portion comprising a hollow tube with a proximal end and a distal end, wherein:
the proximal support structure and the distal support structure are of a polymeric material,
the proximal support structure has a stiffness that is higher than a stiffness of the distal support structure,
the first connector comprises a first hollow joint protruding from the first middle section towards the waist portion,
the second connector comprises a second hollow joint protruding from the second middle section towards the waist portion,
the proximal support structure and the distal support structure are detachably connectable to the waist portion such that the first hollow joint of the proximal support structure is configured to be inserted into the proximal end of the hollow tube and the second hollow joint of the distal support structure is configured to be inserted into the distal end of the hollow tube, and
the first hollow joint of the proximal support structure is integrally provided together with the at least two arms of the proximal support structure and the second hollow joint of the distal support structure is integrally provided together with the at least three arms of the distal support structure.

31. The occlusion device according to claim 30, wherein the proximal occlusion film is supported by the at least two arms of the proximal support structure.

32. The occlusion device according to claim 30, further comprising reinforcing members for strengthening the proximal support structure.

33. The occlusion device according to claim 32, wherein the reinforcing members are at least two reinforcing films each extending from an end of the waist portion, which is connected to the distal support structure, to the proximal occlusion film supported by the at least two arms of the proximal support structure.

34. The occlusion device according to claim 33, wherein each reinforcing film is welded at a respective arm of the at least two arms of the proximal support structure at a position between a center of the proximal support structure and a middle portion of the respective arm.

35. The occlusion device according to claim 30, wherein the proximal support structure comprises two reinforcing films separated from each other by a distance that is not larger than a maximum diameter of the anatomical defect in the tissue.

36. The occlusion device according to claim 30, wherein the at least two arms of the proximal support structure have inner ends that are configured to be folded to be inserted into a sheath in an inward direction.

37. The occlusion device according to claim 30, wherein the at least three arms of the distal support structure are four or more spokes outwardly extending from a middle section of the distal support structure.

38. The occlusion device according to claim 30, wherein the at least three arms of the distal support structure have inner ends configured to be folded to be inserted into a sheath in either an inward or outward direction.

39. The occlusion device according to claim 30, wherein the entire occlusion device is made of the polymeric material.

40. The occlusion device according to claim 39, wherein the polymeric material is a non-biodegradable polymer selected from the group consisting of polyurethane, poly (ether urethanes), poly(ester urethanes), polyvinylchloride, polyalkylenes, polyethylene terephthalate, polyvinylacetate, poly ethylene-co-vinyl acetate and nylon.

41. The occlusion device according to claim 39, wherein the polymeric material is a biodegradable polymer selected from the group consisting of polycaprolactone (PCL), polylactic acid (PLA), polycaprolactone-polylactic acid copolymer (PCL-PLA copolymer), polyglycolide (PGA), poly-L-lactide (PLLA), poly-D-lactide (PDLA), polylactide-polyglycolide copolymer (PLGA), polylactic acid-polyethylene oxide copolymers, polygluconate polyhydroxybutyrate, polyanhydride, polyphosphoester, poly(amino acids), polydioxanone, cellulose, collagen and chitosan.

42. The occlusion device according to claim 30, wherein one or more of the proximal support structure, the proximal occlusion film, the distal support structure, the distal occlusion film, and the waist portion comprises a therapeutically active agent.

43. The occlusion device according to claim 42, wherein the therapeutically active agent is selected from the group consisting of a drug, an antibiotic, an anti-inflammatory agent, an anti-clotting factor, a hormone, a nucleic acid, a peptide, a cellular factor, a growth factor, a ligand for a cell surface receptor, an anti-proliferation agent, an anti-thrombotic agent, an antimicrobial agent, an anti-viral agent, a chemotherapeutic agent, and an anti-hypertensive agent.

44. The occlusion device according to claim 30, wherein one or more of the proximal support structure, the proximal occlusion film, the distal support structure, the distal occlusion film, and the waist portion comprise a radiopacifier.

45. The occlusion device according to claim 30, wherein the proximal support structure, the distal support structure and the waist portion comprise radiopacifiers.

46. The occlusion device according to claim 30, further comprising a delivering system that includes:
   a sheath; and
   at least one first delivering member configured to move the occlusion device through the sheath.

47. The occlusion device according to claim 46, wherein the at least one first delivering member is a rod removably connected to the proximal support structure.

48. The occlusion device according to claim 46, further comprising a second delivering member removably connected to the distal support structure and configured to move the occlusion device through the sheath or to move it back into the sheath.

49. The occlusion device according to claim 48, wherein the second delivering member includes a wire spring having a tip and a connecting member at the tip.

50. The occlusion device according to claim 49, wherein the distal support structure comprises a rear end having a threaded hollow tube with a threaded exterior surface.

51. The occlusion device according to claim 49, wherein the connecting member comprises a threaded interior surface that engages at the threaded hollow tube of the distal support structure.

52. The occlusion device according to claim 51, wherein the hollow tube of the distal support structure comprises a locking member and the at least one first delivering member is a rod removably connected to the proximal support structure and having a protruding member configured to be engaged to twist off the distal support structure from the second delivering member.

53. The occlusion device according to claim 30 provided in a sterilized package.

54. A method of closing an anatomical defect in a tissue, the anatomical defect including an opening connecting a front side and a back side of the tissue, comprising the steps of:
   providing a sheath into which the occlusion device according to claim 1 has been inserted,
   moving the occlusion device through the sheath to the anatomical defect,
   moving the proximal support structure of the occlusion device out of the sheath through the anatomical defect to the front side of the tissue,
   deploying the proximal support structure at the front side of the tissue to close the defect from the front side,
   withdrawing the sheath to release the waist portion of the occlusion device in the opening and to release the distal support structure and the waist portion at the back side of the tissue, and
   deploying the distal support structure of the occlusion device at the anatomical defect to close the anatomical defect from the back side of the tissue.

55. The method according to claim 54, comprising moving the sheath through the opening while moving the proximal support structure out of the sheath.

56. The method according to claim 54, comprising deploying the sheath at the front side of the anatomical defect while moving the proximal support structure out of the sheath.

57. The method according to claim 54, wherein the occlusion device is a first occlusion device, the method further comprising retrieving the first occlusion device out of the sheath and using a second occlusion device in a next step.

58. The method according to claim 57, wherein retrieving the occlusion device comprises withdrawing a retrieval wire while holding the sheath in position to force either the proximal support structure and/or the distal support structure of the first occlusion device into the sheath or comprises withdrawing a delivering member connected to the support structure to force either all of the first occlusion device or the distal support structure into the sheath.

59. The method according to claim 54, wherein the anatomical defect in the tissue is a septal defect or shunt in a heart or a vascular system.

60. The method according to claim 59, wherein the septal defect is selected from the group consisting of atrial septal defects, ventricular septal defects, patent ductus arteriosus, and patent foramen ovale.

* * * * *